(12) United States Patent
Tanaka

(10) Patent No.: US 11,783,622 B2
(45) Date of Patent: Oct. 10, 2023

(54) FINGERPRINT AUTHENTICATION DEVICE AND FINGERPRINT AUTHENTICATION METHOD

(71) Applicant: SONY GROUP CORPORATION, Tokyo (JP)

(72) Inventor: Yu Tanaka, Tokyo (JP)

(73) Assignee: SONY GROUP CORPORATION, Tokyo (JP)

( * ) Notice: Subject to any disclaimer, the term of this patent is extended or adjusted under 35 U.S.C. 154(b) by 0 days.

(21) Appl. No.: 17/641,901

(22) PCT Filed: Sep. 4, 2020

(86) PCT No.: PCT/JP2020/033611
§ 371 (c)(1),
(2) Date: Mar. 10, 2022

(87) PCT Pub. No.: WO2021/054151
PCT Pub. Date: Mar. 25, 2021

(65) Prior Publication Data
US 2022/0327859 A1 Oct. 13, 2022

(30) Foreign Application Priority Data
Sep. 18, 2019 (JP) .................. 2019-169092

(51) Int. Cl.
*G06V 40/12* (2022.01)
*G06V 40/60* (2022.01)
*G06V 40/50* (2022.01)

(52) U.S. Cl.
CPC .......... *G06V 40/1335* (2022.01); *G06V 40/67* (2022.01); *G06V 40/1365* (2022.01); *G06V 40/50* (2022.01)

(58) Field of Classification Search
CPC ............... G06V 40/1335; G06V 40/67; G06V 40/1365; G06V 40/50; A61B 5/1172; G06F 3/0481; G06T 1/00
See application file for complete search history.

(56) References Cited

U.S. PATENT DOCUMENTS

2004/0184027 A1   9/2004   Mizutani et al.
2015/0074615 A1*  3/2015   Han .................... H04L 63/0861
                                                            715/863
(Continued)

FOREIGN PATENT DOCUMENTS

CN        1527243 A        9/2004
CN      104850821 A        8/2015
(Continued)

OTHER PUBLICATIONS

International Search Report and Written Opinion of PCT Application No. PCT/JP2020/033611, dated Oct. 20, 2020, 09 pages of ISRWO.

Primary Examiner — Premal R Patel
(74) Attorney, Agent, or Firm — CHIP LAW GROUP

(57) ABSTRACT

Provided are a fingerprint authentication device and a fingerprint authentication method capable of efficiently performing registration of fingerprint information or authentication of a fingerprint. A presentation image that presents a position of a fingernail root at a time of detecting the fingerprint is generated, and an image of the fingerprint is obtained using the generated presentation image.

17 Claims, 29 Drawing Sheets

(56) References Cited

U.S. PATENT DOCUMENTS

| | | |
|---|---|---|
| 2015/0135108 A1 | 5/2015 | Pope et al. |
| 2015/0235098 A1 | 8/2015 | Lee et al. |
| 2018/0114047 A1* | 4/2018 | Kim .................. G06V 40/1335 |
| 2020/0092411 A1* | 3/2020 | Xu .................... H04M 1/72469 |

FOREIGN PATENT DOCUMENTS

| | | |
|---|---|---|
| CN | 106133748 A | 11/2016 |
| EP | 2911091 A2 | 8/2015 |
| JP | 3-180988 A | 8/1991 |
| JP | 2004-272322 A | 9/2004 |
| JP | 2007-310639 A | 11/2007 |
| JP | 2015-022713 A | 2/2015 |
| JP | 2018-195316 A | 12/2018 |
| KR | 10-2004-0078911 A | 9/2004 |
| KR | 10-2015-0021943 A | 3/2015 |
| KR | 10-2015-0098158 A | 8/2015 |
| TW | 200426699 A | 12/2004 |

\* cited by examiner

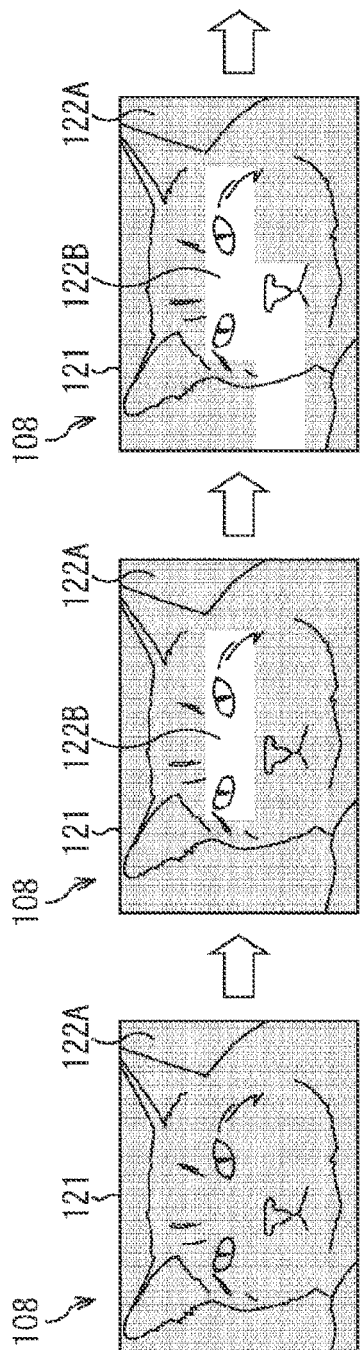
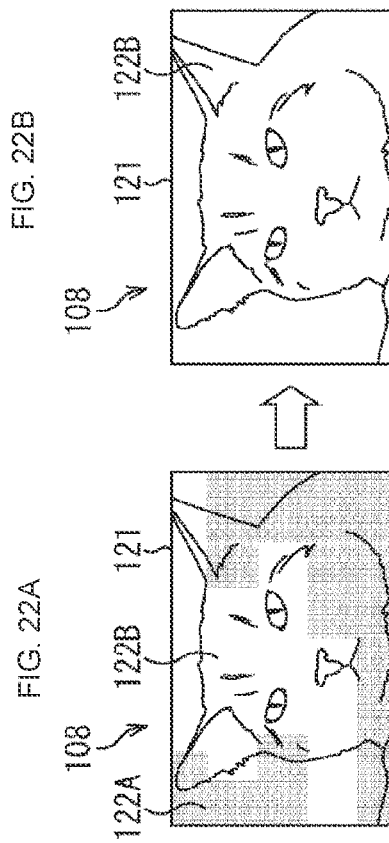
FIG. 22A
FIG. 22B
FIG. 22C
FIG. 22D
FIG. 22E

FINGERPRINT AUTHENTICATION DEVICE AND FINGERPRINT AUTHENTICATION METHOD

CROSS REFERENCE TO RELATED APPLICATIONS

This application is a U.S. National Phase of International Patent Application No. PCT/JP2020/033611 filed on Sep. 4, 2020, which claims priority benefit of Japanese Patent Application No. JP 2019-169092 filed in the Japan Patent Office on Sep. 18, 2019. Each of the above-referenced applications is hereby incorporated herein by reference in its entirety.

TECHNICAL FIELD

The present technology relates to a fingerprint authentication device, a fingerprint authentication method, and a program, and more particularly, to a fingerprint authentication device, a fingerprint authentication method, and a program that efficiently perform registration of fingerprint information or authentication of a fingerprint.

BACKGROUND ART

Patent Document 1 discloses displaying a fingerprint registration interface, detecting multiple finger gestures performed by a finger on a fingerprint sensor, and collecting fingerprint information from the multiple finger gestures.

CITATION LIST

Patent Document

Patent Document 1: Japanese Patent Application Laid-Open No. 2018-195316

SUMMARY OF THE INVENTION

Problems to be Solved by the Invention

It is desired to efficiently perform registration of fingerprint information or authentication of a fingerprint.

The present technology has been conceived in view of such a situation, and makes it possible to efficiently perform registration of fingerprint information or authentication of a fingerprint.

Solutions to Problems

A fingerprint authentication device or a program according to one aspect of the present technology is directed to a fingerprint authentication device including a display control unit that generates a presentation image for presenting a position of a nail root of a finger at a time of obtaining an image of a fingerprint and a processing unit that obtains the image of the fingerprint using the generated presentation image, or to a program for causing a computer to function as such a fingerprint authentication device.

A fingerprint authentication method according to one aspect of the present technology is directed to a fingerprint authentication method for a fingerprint authentication device including a display control unit and a processing unit, the method including generating, using the display control unit, a presentation image for presenting a position of a nail root of a finger at a time of obtaining an image of a fingerprint, and obtaining, using the processing unit, the image of the fingerprint using the generated presentation image.

According to a fingerprint authentication device, a fingerprint authentication method, and a program according to one aspect of the present technology, a presentation image that presents a position of a nail root of a finger at a time of obtaining an image of a fingerprint is generated, and an image of the fingerprint is obtained using the generated presentation image.

BRIEF DESCRIPTION OF DRAWINGS

FIGS. 22A, 22B, 22C, 22D and 22E are diagrams exemplifying a third mode of the acquisition status image that presents an acquisition status of the feature amount.

MODE FOR CARRYING OUT THE INVENTION

Hereinafter, an embodiment of the present technology will be described with reference to the drawings.

Embodiment of Fingerprint Authentication Device

Figure 1:
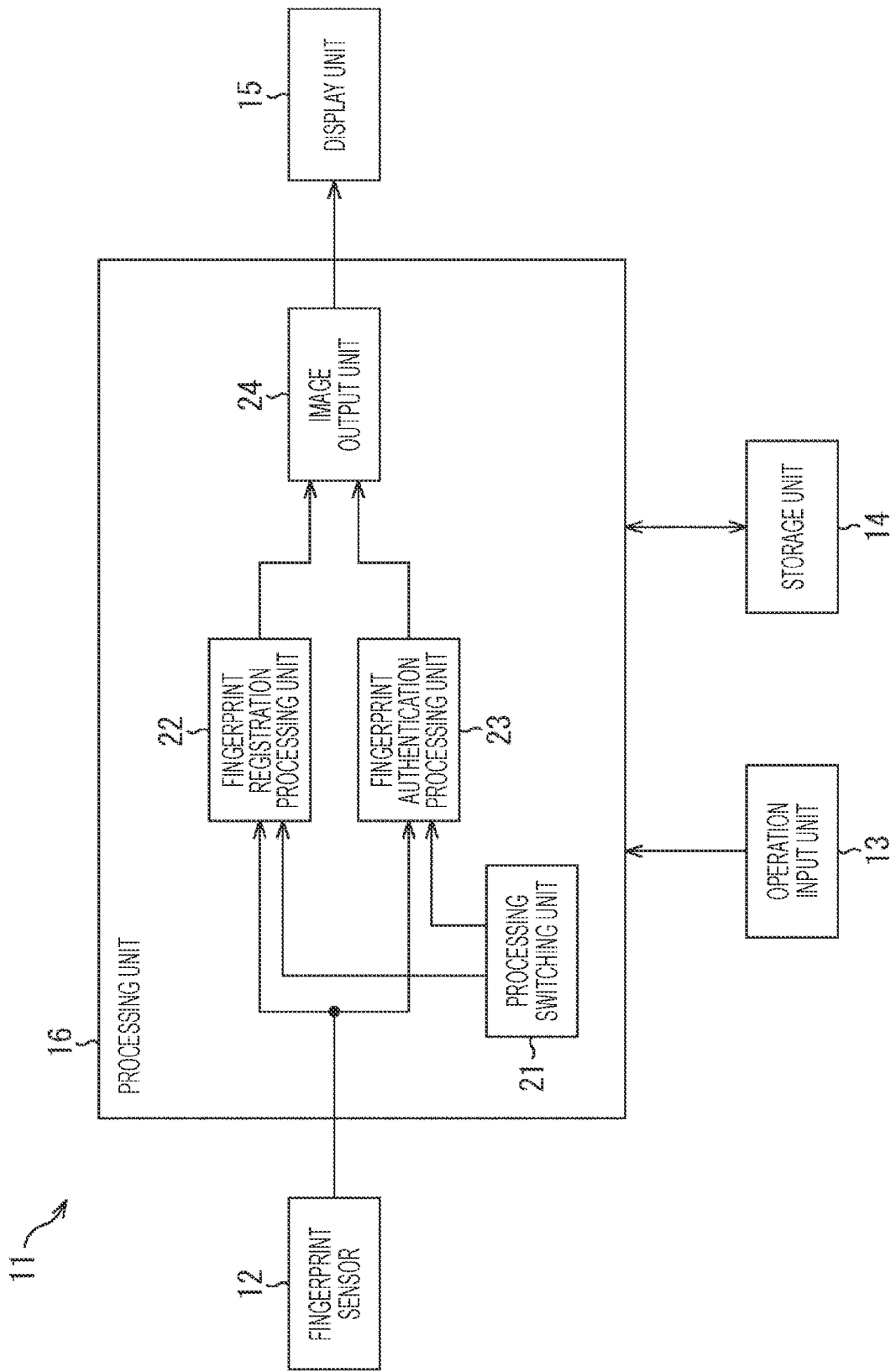
FIG. 1 is a block diagram illustrating an exemplary configuration of a fingerprint authentication device according to an embodiment to which the present technology is applied.

FIG. 1 is a block diagram illustrating an exemplary configuration of a fingerprint authentication device according to an embodiment to which the present technology is applied.

A fingerprint authentication device 11 of FIG. 1 is installed in, for example, a wearable device such as a smartphone or a wristband-type device, or a device such as a tablet terminal. The fingerprint authentication device 11 includes a fingerprint sensor 12, an operation input unit 13, a storage unit 14, a display unit 15, and a processing unit 16.

The fingerprint sensor 12 detects a fingerprint in contact with a detection area (detection plane). Specifically, the fingerprint sensor 12 obtains an image of a fingerprint (fingerprint image) in a range in contact with the detection area, and supplies it to the processing unit 16. The fingerprint sensor 12 may be any type such as an optical type, an electrostatic type, and an ultrasonic type. Note that, as an optical fingerprint sensor, there has been known a fingerprint sensor that irradiates a fingerprint placed on the detection area with light, collects light reflected by the fingerprint with a microlens array, and photoelectrically converts the light with an imaging element to obtain a fingerprint image.

Figure 2:
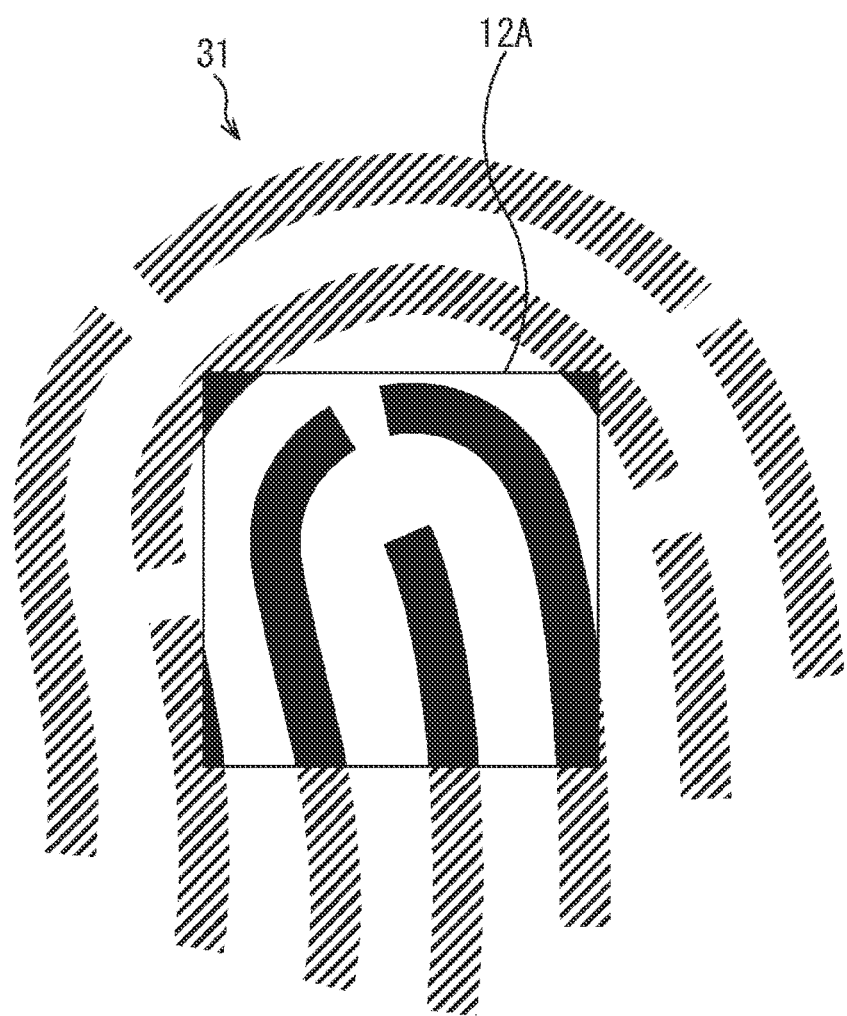
FIG. 2 is a diagram comparing sizes of a range of a detection area of a fingerprint sensor and a range of a fingerprint.

Furthermore, the fingerprint sensor 12 is a small-area sensor in which a detection area for detecting a fingerprint is small relative to the substantially entire range of the fingerprint (hereinafter referred to as an entire range of a fingerprint). FIG. 2 is a diagram comparing sizes of the detection area of the fingerprint sensor 12 and the entire range of the fingerprint. In FIG. 2, a vertical width and horizontal width of a detection area 12A of the fingerprint sensor 12 are set to be lengths of approximately ¼ to ½ of a vertical width and horizontal width of the entire range of a fingerprint 31, respectively. Therefore, the range of the fingerprint image that can be captured by the fingerprint sensor 12 at one time is a part of the entire range of the fingerprint 31. A fingerprint image of the entire range of the fingerprint 31 can be obtained by changing the contact portion of the fingerprint 31 with respect to the detection area 12A and capturing a fingerprint image multiple times. Note that the present technology is applicable even if the fingerprint sensor 12 is not a small-area sensor.

In FIG. 1, the operation input unit 13 is, for example, a touch panel or an operation button, and supplies a user operation performed by a user to the processing unit 16.

The storage unit 14 stores information supplied from the processing unit 16, and furthermore, supplies the stored information to the processing unit 16. For example, the storage unit 14 stores fingerprint information of the user to be registered in the fingerprint authentication device 11.

The display unit 15 displays an image represented by image signals supplied from the processing unit 16 on a display. Note that the display unit 15 may be a display unit in a device connected to the fingerprint authentication device 11 via communication such as Bluetooth (registered trademark), or may be a plurality of separate display units.

The processing unit 16 executes various types of processing by executing a program. The processing unit 16 includes a processing switching unit 21, a fingerprint registration processing unit 22, a fingerprint authentication processing unit 23, and an image output unit 24 as functional blocks to be implemented by program execution.

In a case where a user operation for registering a fingerprint is performed on the operation input unit 13, the processing switching unit 21 disables the processing of the fingerprint authentication processing unit 23, and enables the processing of the fingerprint registration processing unit 22. On the other hand, in a case where a user operation for performing fingerprint authentication is performed on the operation input unit 13, it disables the processing of the fingerprint registration processing unit 22, and enables the processing of the fingerprint authentication processing unit 23.

The fingerprint registration processing unit 22 performs a process of registering a user fingerprint (fingerprint registration process). That is, in a case of registering a user fingerprint, the fingerprint registration processing unit 22 obtains a feature amount of the fingerprint as fingerprint information associated with the fingerprint on the basis of the fingerprint image from the fingerprint sensor 12, and creates a template (standard pattern) to be used for fingerprint authentication. Then, the fingerprint registration processing unit 22 causes the storage unit 14 to store the created template.

Furthermore, the fingerprint registration processing unit 22 generates a finger position presentation image that presents a finger position at the time of obtaining a fingerprint image using the fingerprint sensor 12 and an acquisition status image that presents an acquisition status of fingerprint information (feature amount), and supplies them to the image output unit 24.

The fingerprint authentication processing unit 23 performs a process of fingerprint authentication (fingerprint authentication process). That is, in a case of performing fingerprint authentication, the fingerprint authentication processing unit 23 collates the fingerprint information detected from the fingerprint image from the fingerprint sensor 12 with the template stored in the storage unit 14. In a case where the fingerprint information detected from the fingerprint image matches the template by the collation, the fingerprint authentication processing unit 23 determines that the user authentication has succeeded. On the other hand, in a case where the fingerprint information detected from the fingerprint image does not match the template, the fingerprint authentication processing unit 23 determines that the user authentication has failed. The device equipped with the fingerprint authentication device 11 executes processing according to the result of the authentication by the fingerprint authentication processing unit 23, that is, the success or failure of the authentication.

Furthermore, the fingerprint authentication processing unit 23 generates a finger position presentation image that presents the finger position at the time of obtaining the fingerprint image using the fingerprint sensor 12, and supplies it to the image output unit 24.

The image output unit 24 functions as a display control unit that generates image signals in a predetermined format for causing the display unit 15 to display the image from the fingerprint registration processing unit 22 or the fingerprint authentication processing unit 23 and supplies them to the display unit 15 to perform display control for displaying the image represented by the image signals.

First Exemplary Device Equipped with Fingerprint Authentication Device 11

Figure 3:
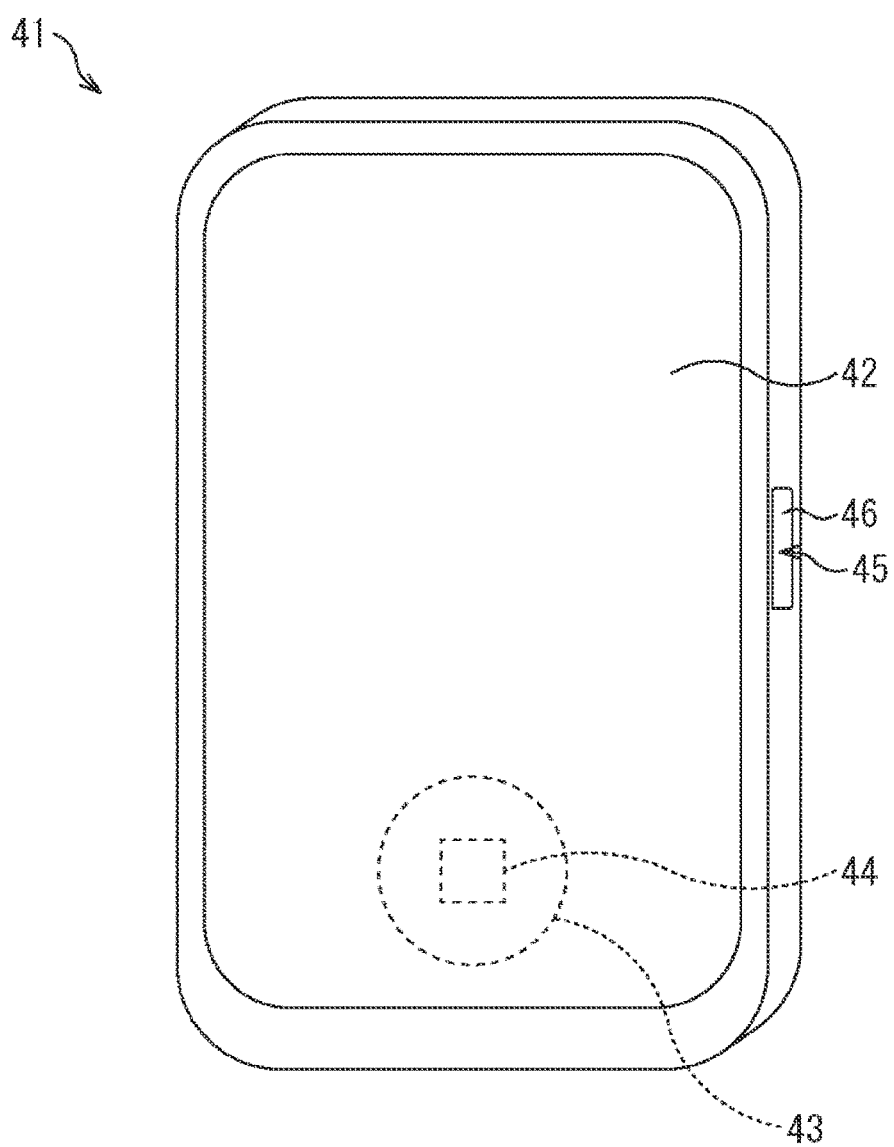
FIG. 3 is a perspective view exemplifying an appearance of a smartphone-type device equipped with the fingerprint authentication device.

FIG. 3 is a perspective view exemplifying an appearance of a smartphone-type device equipped with the fingerprint authentication device 11. In FIG. 3, a smartphone-type device 41 includes a display 42 with a touch panel and a fingerprint sensor 43. The display 42, the touch panel, and the fingerprint sensor 43 correspond to the display unit 15, the operation input unit 13, and the fingerprint sensor 12 in FIG. 1, respectively.

In FIG. 3, the display 42 is provided on a front face of a rectangular housing. The display 42 is, for example, an organic light-emitting diode (OLED) display or a liquid crystal display, and includes a touch panel.

The fingerprint sensor 43 is embedded in the display 42. The fingerprint sensor 43 is, for example, an optical sensor including an imaging unit, and captures a fingerprint of a finger in contact with the surface of the detection area 44 using the imaging unit (not illustrated) to obtain a fingerprint image. However, the fingerprint sensor 43 may be a sensor of another type such as an ultrasonic type.

Furthermore, the fingerprint sensor 43 is a small-area sensor in which the detection area 44 is smaller than the entire range of the fingerprint as illustrated in FIG. 2.

Furthermore, in the smartphone-type device 41, a fingerprint sensor 45 may be provided on a side surface or the like (a part other than the display 42) of the housing instead of the fingerprint sensor 43 embedded in the display 42. The fingerprint sensor 45 corresponds to the fingerprint sensor 12 in FIG. 1, and is a small-area sensor in which a detection area 46 is smaller than the entire range of the fingerprint. That is, the fingerprint sensor 12 in FIG. 1 may not be embedded in the display unit 15, and may not include the display unit 15 capable of displaying an image superimposed on the detection area 12A.

Second Exemplary Device Equipped with Fingerprint Authentication Device 11

Figure 4:
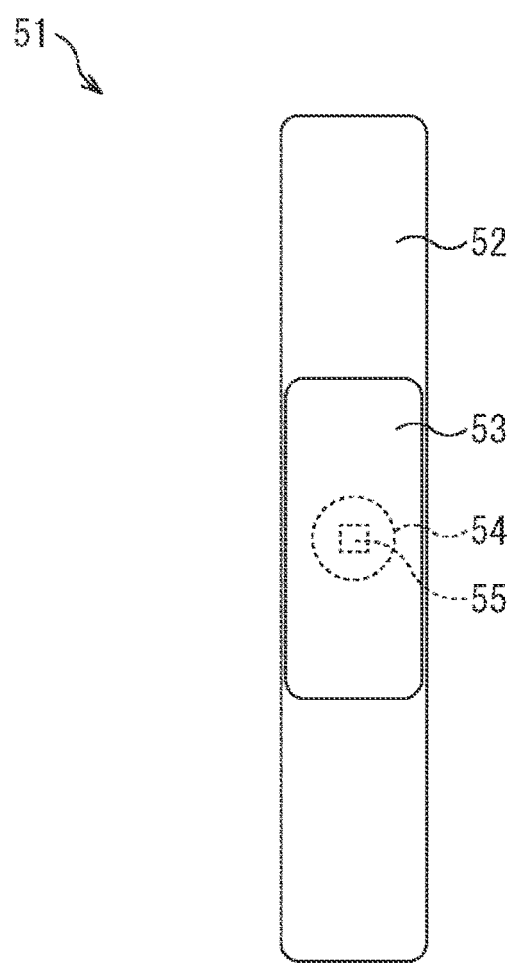
FIG. 4 is a front view exemplifying an appearance of a wristband-type device equipped with the fingerprint authentication device.

FIG. 4 is a front view exemplifying an appearance of a wristband-type device equipped with the fingerprint authentication device 11. In FIG. 4, a wristband-type device 51 includes a band 52, a display 53, and a fingerprint sensor 54. The display 53 and the fingerprint sensor 54 correspond to the display unit 15 and the fingerprint sensor 12 in FIG. 1, respectively.

In FIG. 4, the band 52 is in a band shape, and is worn by the user by being wound around a wrist or the like.

The display 53 is, for example, an OLED display or a liquid crystal display, and is provided on the inner peripheral surface or the outer peripheral surface of the band 52.

The fingerprint sensor 54 is embedded in the display 53. The fingerprint sensor 54 is, for example, an optical sensor including an imaging unit, and captures a fingerprint of a finger in contact with a surface of a detection area 55 using the imaging unit (not illustrated) to obtain a fingerprint image. However, the fingerprint sensor 54 may be a sensor of another type such as an ultrasonic type. Furthermore, the fingerprint sensor 54 is a small-area sensor.

Exemplary Configuration of Fingerprint Registration Processing Unit 22

Figure 5:
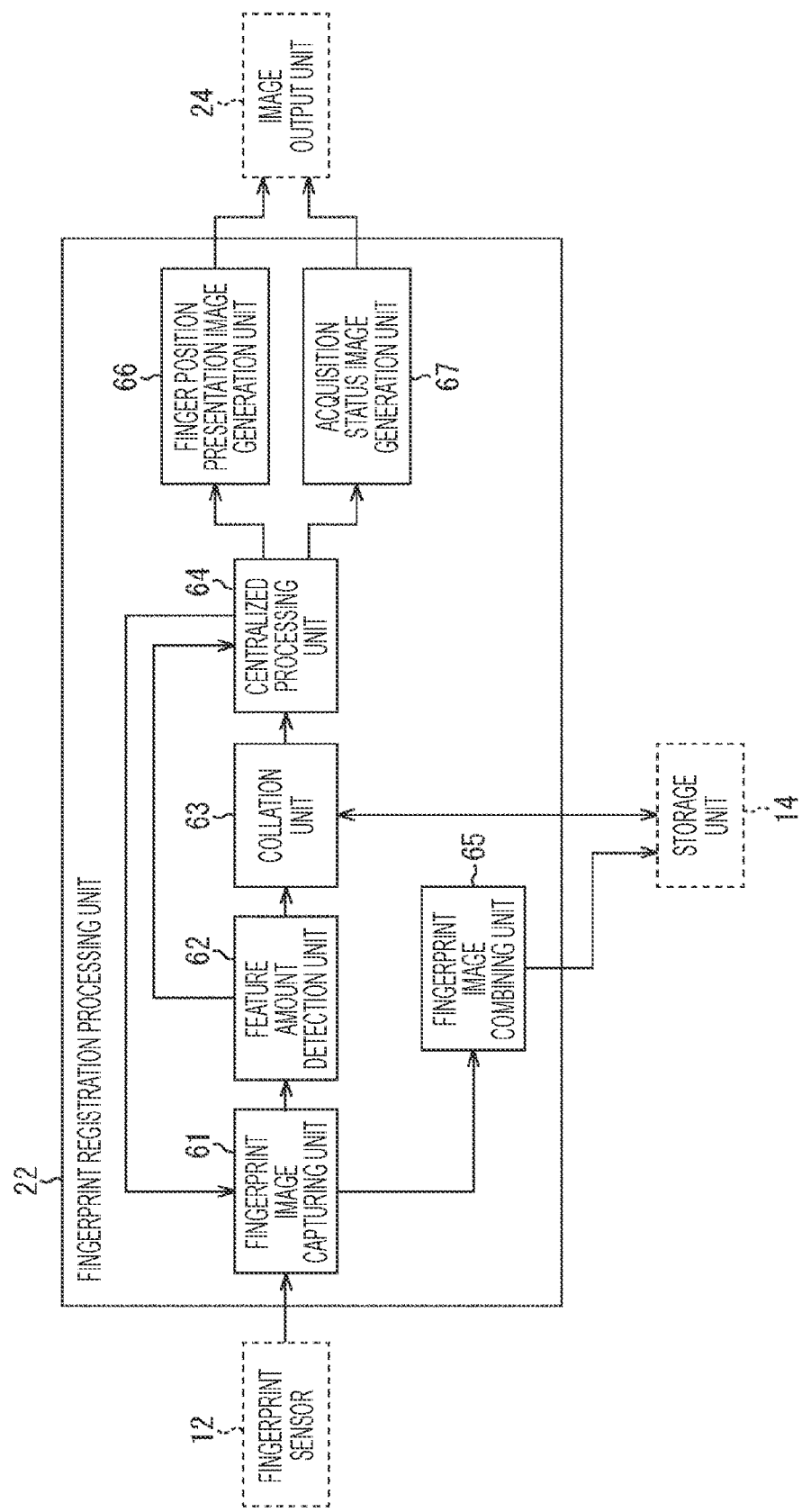
FIG. 5 is a block diagram illustrating an exemplary configuration of a fingerprint registration processing unit in FIG. 1.

FIG. 5 is a block diagram illustrating an exemplary configuration of the fingerprint registration processing unit 22 in FIG. 1.

In FIG. 5, the fingerprint registration processing unit 22 includes a fingerprint image capturing unit 61, a feature amount detection unit 62, a collation unit 63, a centralized processing unit 64, a fingerprint image combining unit 65, a finger position presentation image generation unit 66, and an acquisition status image generation unit 67.

The fingerprint image capturing unit 61 captures (obtains) a fingerprint image from the fingerprint sensor 12 on the basis of an instruction from the centralized processing unit 64, and supplies it to the feature amount detection unit 62 and to the fingerprint image combining unit 65.

The feature amount detection unit 62 extracts multiple feature points (minutiae) included in the fingerprint on the basis of the fingerprint image from the fingerprint image capturing unit 61, and detects a feature amount indicating a position and a direction of each feature point as fingerprint information. The feature amount detection unit 62 supplies the detected feature amount to the collation unit 63.

The collation unit 63 registers a feature amount not registered as a template among the feature amounts from the feature amount detection unit 62 as a template in the storage unit 14. That is, the collation unit 63 collates the feature amount registered as a template with the feature amount from the feature amount detection unit 62. Then, the collation unit 63 registers a feature amount not registered as a template among the feature amounts from the feature amount detection unit 62 as a template in the storage unit 14.

Furthermore, in a case where a degree of matching between the feature amount registered as a template and the feature amount from the feature amount detection unit 62 is equal to or higher than a predetermined threshold value, for example, the collation unit 63 determines that the feature amount registered as a template and the feature amount from the feature amount detection unit 62 match with each other. On the other hand, in a case where the degree of matching between the feature amount registered as a template and the feature amount from the feature amount detection unit 62 is less than the threshold value, the collation unit 63 determines that the feature amount registered as a template and the feature amount from the feature amount detection unit 62 do not match with each other. Then, the collation unit 63 supplies a collation result as to whether the feature amount registered as a template and the feature amount from the feature amount detection unit 62 match with each other to the centralized processing unit 64.

Each time a collation result is supplied from the collation unit 63, the centralized processing unit 64 instructs the fingerprint image capturing unit 61 to capture a new fingerprint image from the fingerprint sensor 12. Furthermore, the centralized processing unit 64 instructs the finger position presentation image generation unit 66 to change the finger position to be presented to the user using a finger position presentation image on the basis of the collation result from the collation unit 63. Moreover, the centralized processing unit 64 supplies, to the acquisition status image generation unit 67, the acquisition status of the feature amount in the feature amount detection unit 62.

The fingerprint image combining unit 65 synthesizes (combines) fingerprint images obtained from different portions of the entire range of the fingerprint, which are fingerprint images from the fingerprint image capturing unit 61, to generate a fingerprint image of the entire range of the fingerprint. The fingerprint image combining unit 65 causes the storage unit 14 to store the combined fingerprint image. Note that the fingerprint image is not necessarily stored, and the fingerprint image combining unit 65 is not necessarily provided.

The finger position presentation image generation unit 66 generates a finger position presentation image that presents the finger position at the time of obtaining the fingerprint image using the fingerprint sensor 12, and supplies it to the image output unit 24. Furthermore, in a case where an instruction to change the finger position is issued by the centralized processing unit 64, the finger position presentation image generation unit 66 generate a finger position presentation image in which the finger position to be presented is changed, and supplies it to the image output unit 24. Note that the finger position presentation image generation unit 66 generates information to be displayed on the display unit 15 even in a case of information other than a finger position presentation image 71, and supplies it to the image output unit 24.

The acquisition status image generation unit 67 generates an acquisition status image that presents the acquisition status of the feature amount to the user on the basis of the acquisition status of the feature amount from the centralized processing unit 64, and supplies it to the image output unit 24.

<Processing Details of Fingerprint Registration Processing Unit 22>

Next, a fingerprint registration process in the fingerprint registration processing unit 22 will be detailed.

Figure 6:
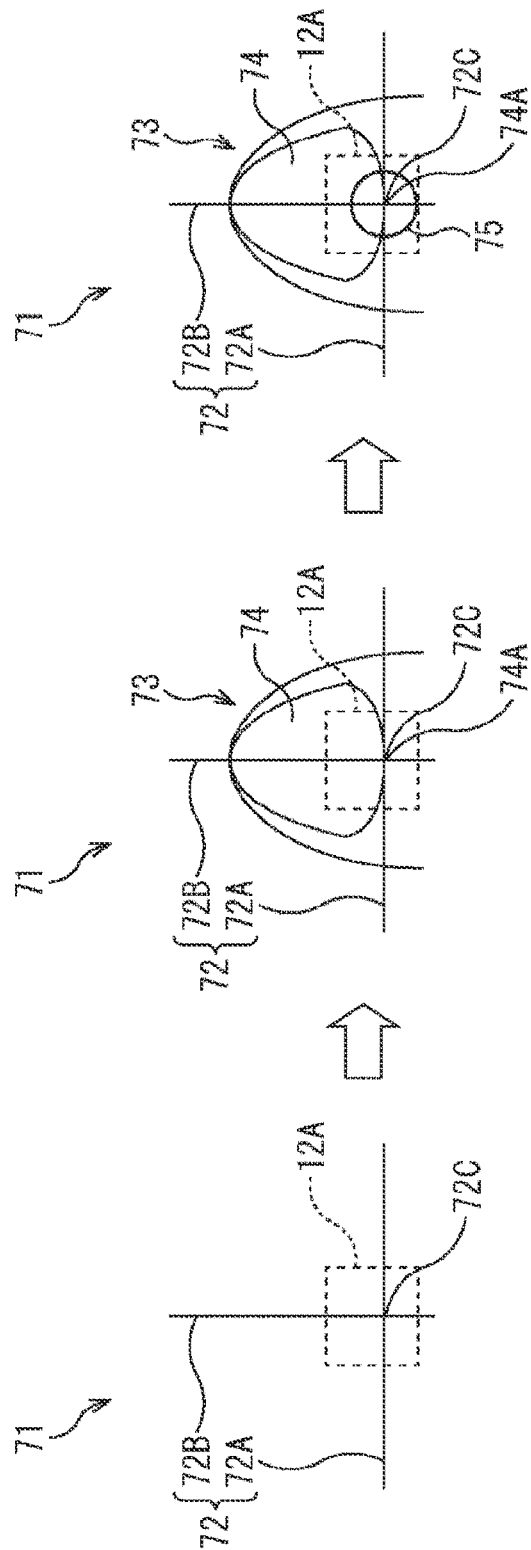
FIGS. 6A, 6B and 6C are diagrams exemplifying a finger position presentation image to be displayed on a display unit when a fingerprint registration process starts.

FIGS. 6A, 6B and 6C are diagrams exemplifying a finger position presentation image to be displayed on the display unit 15 when the fingerprint registration process starts. FIGS. 6A, 6B and 6C illustrate the finger position presentation image 71 sequentially displayed on the display unit 15 immediately after the start of the fingerprint registration process.

Note that the finger position presented by the finger position presentation image is sequentially changed from a predetermined first finger position to an M-th (M is an integer of 2 or more) finger position. The finger position presentation image 71 in FIGS. 6A, 6B and 6C presents the first finger position.

In FIG. 6A, the finger position presentation image 71 is a cross image 72 in a shape of a cross in which a horizontal line 72A intersects with a vertical line 72B. A finger position reference point 72C is an intersecting point of the horizontal line 72A and the vertical line 72B. The cross image 72 is displayed at a position where the finger position reference point 72C is at a substantially central position of the detection area 12A of the fingerprint sensor 12. Note that a broken line frame indicating the detection area 12A is not displayed on the display unit 15.

A fingertip image 73 is added to the finger position presentation image 71 in FIG. 6B displayed on the display unit 15 subsequent to FIG. 6A in a manner of being superimposed on the cross image 72. The fingertip image 73 includes an outline of the fingertip and a nail image 74. A nail root 74A is a boundary portion between a portion of the nail exposed to the outside and a skin portion, which indicates an intermediate position in the width direction of the nail (finger). Then, the fingertip image 73 is displayed in such a manner that the nail root 74A coincides with the finger position reference point 72C in the cross image 72.

A circle mark 75 is added to the finger position presentation image 71 in FIG. 6C displayed on the display unit 15 subsequent to FIG. 6B in a manner of being superimposed on the cross image 72 and the fingertip image 73. The circle mark 75 is a circular image centered on the finger position reference point 72C of the cross image 72.

First, in FIG. 6A, the cross image 72 is displayed to present a position that the user is to be prompted to touch.

Subsequently, in FIG. 6B, the fingertip image 73 is displayed to prompt the user to touch the position of the cross image 72 in such a manner that the nail root is located at the finger position reference point 72C of the cross image 72. The back side of the nail root is a substantially central position of the fingerprint regardless of individual differences such as a finger size, and is an important portion where the density of the feature points (minutiae) of the fingerprint is higher. With the nail root aligned with the position of the finger position reference point 72C, it becomes possible to align the substantially central position of the fingerprint with the position of the finger position reference point 72C regardless of individual differences such as a finger size.

Furthermore, the orientation of the fingertip at the time of touching the detection area 12A is presented to the user by the fingertip image 73. That is, it is prompted to touch the position of the cross image 72 in such a manner that the direction of the central axis of the fingertip matches the direction of the vertical line 72B of the cross image 72 and the width direction of the fingertip matches the direction of the horizontal line 72A of the cross image 72.

Subsequently, in FIG. 6C, the circle mark 75 is displayed in such a manner that the position of the finger position reference point 72C is emphasized, whereby it becomes possible to cause the user to recognize that it is important to align the nail root with the finger position reference point 72C.

With such presentation of the finger position using the finger position presentation image 71, it becomes possible to cause the user to touch with the nail root aligned with the position of the finger position reference point 72C with high reproducibility regardless of the user, and to touch the position of the finger position reference point 72C at the central position of the fingerprint.

Note that, in other words, the finger position presentation image 71 is a presentation image presenting a nail root position.

When the fingerprint registration process starts in the fingerprint registration processing unit 22, the finger position presentation image generation unit 66 in FIG. 5 sequentially generates the finger position presentation images 71 of FIGS. 6A, 6B and 6C, supplies them to the image output unit 24, and causes the display unit 15 to display them.

Figure 7:
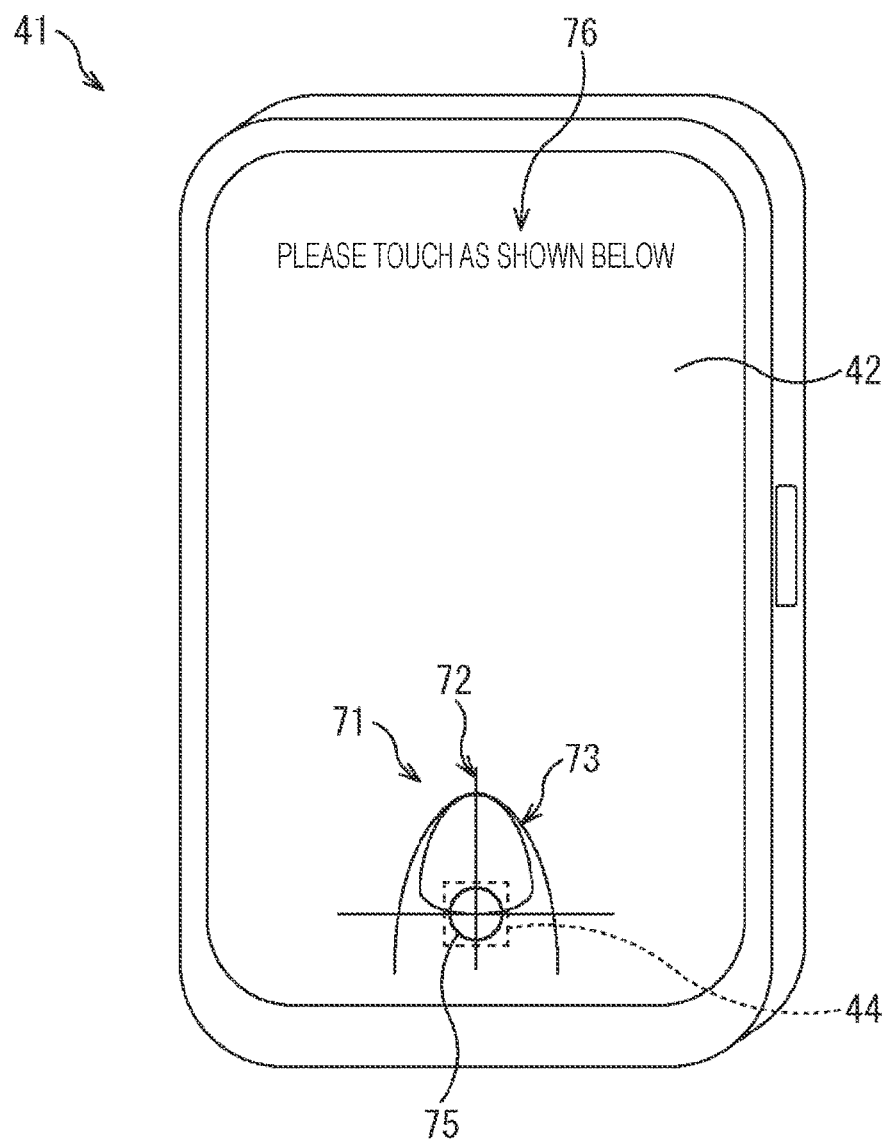
FIG. 7 is a diagram illustrating exemplary display of the finger position presentation image in a case of the smartphone-type device illustrated in FIG. 3 in which a fingerprint sensor is embedded in a display.

Here, FIG. 7 is a diagram illustrating exemplary display of the finger position presentation image 71 in a case of the smartphone-type device 41 of FIG. 3 equipped with the fingerprint authentication device 11 in which the fingerprint sensor 43 (not illustrated in FIG. 7) is embedded in the display 42.

In FIG. 7, the finger position presentation image 71 is displayed on the display 42 at the position of the detection area 44 of the fingerprint sensor 43 (see FIG. 3) embedded in the display 42. Note that an image of a broken line indicating the detection area 44 is not displayed. Furthermore, as in FIGS. 6A, 6B and 6C, the cross image 72, the fingertip image 73, and the circle mark 75 are superimposed and displayed in a stepwise manner at the start of the fingerprint registration process. Moreover, guidance information 76 of "please touch as shown below" is displayed on the display 42 together with the finger position presentation image 71. The finger position presentation image generation unit 66 of FIG. 5 generates an image including the finger position presentation image 71 and the guidance information 76 to be displayed on the display 42 in this manner, and supplies it to the image output unit 24.

Figure 8:
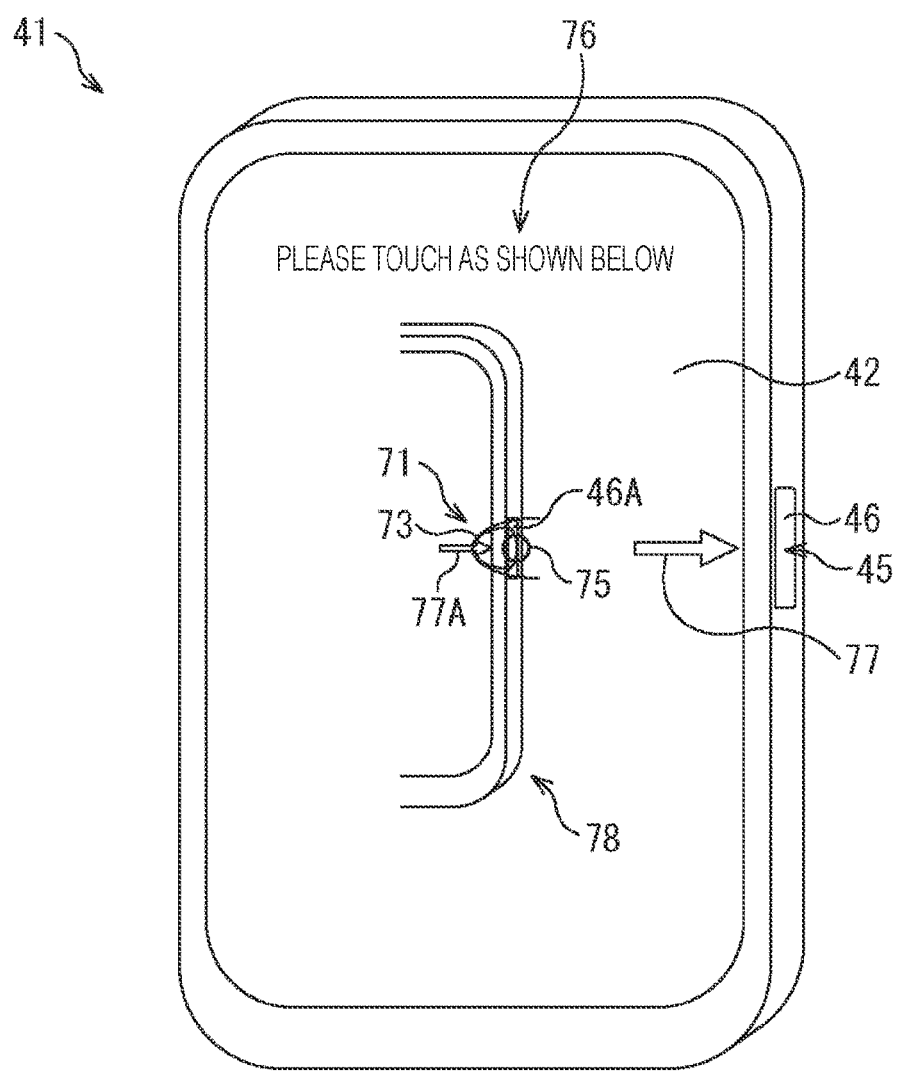
FIG. 8 is a diagram illustrating exemplary display of the finger position presentation image in a case of the smartphone-type device illustrated in FIG. 3 in which the fingerprint sensor is embedded in a part other than the display.

FIG. 8 is a diagram illustrating exemplary display of the finger position presentation image 71 in a case of the smartphone-type device 41 illustrated in FIG. 3 in which the fingerprint sensor 45 is embedded in a part other than the display 42.

In FIG. 8, an appearance image 78 imitating an appearance of a partial range of the smartphone-type device 41, that is, a part including a right-side surface provided with the fingerprint sensor 45 is displayed on the display 42. Furthermore, an arrow image 77 indicating a position where the detection area 46 of the fingerprint sensor 45 is provided is displayed on the display 42, and an arrow image 77A indicating a position of a detection area 46A corresponding to the detection area 46 is also displayed in the appearance image 78. Then, the finger position presentation image 71 is displayed at the position of the detection area 46A in the appearance image 78. Note that the cross image 72 of FIGS. 6A, 6B and 6C is not displayed in the finger position presentation image 71 of FIG. 8. The arrow images 77 and 77A, the fingertip image 73, and the circle mark 75 are superimposed and displayed in a stepwise manner at the start of the fingerprint registration process.

The finger position presentation image 71 of FIG. 8 presents the finger position with respect to the detection area 46A in the appearance image 78, thereby indirectly presenting the finger position with respect to the detection area 46 of the fingerprint sensor 45. Furthermore, the finger position presentation image 71 displayed in the appearance image 78 is an image obtained by being rotated counterclockwise by 90 degrees with respect to the finger position presentation image 71 in FIG. 6C, and indicates that the orientation of the fingertip at the time of touching the detection area 46 is set in the lateral direction. Moreover, the guidance information 76 of "please touch as shown below" is displayed on the display 42. Note that the cross image 72 may be displayed also in the finger position presentation image 71 of FIG. 8.

The finger position presentation image generation unit 66 of FIG. 5 generates an image including the arrow images 77 and 77A, the appearance image 78, and the finger position presentation image 71 to be displayed on the display 42 in this manner, and supplies it to the image output unit 24.

Figure 9:
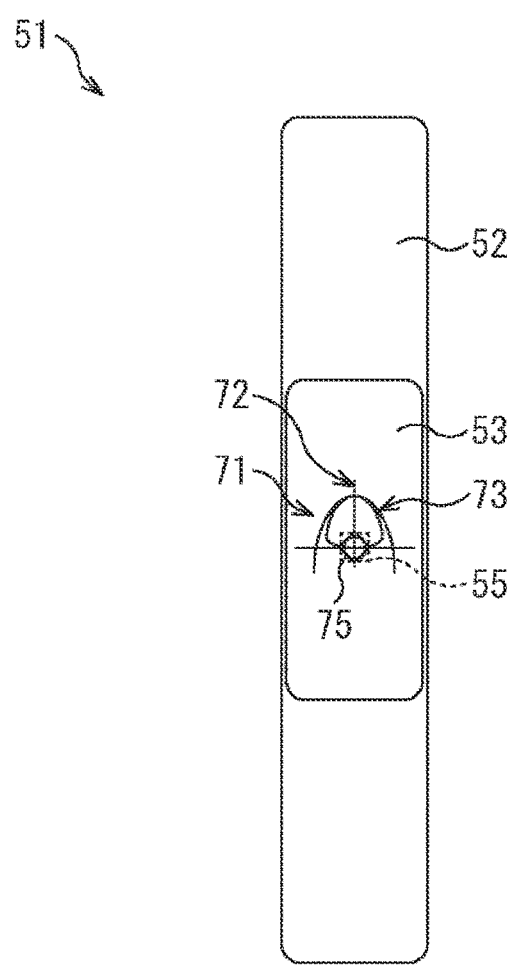
FIG. 9 is a diagram illustrating exemplary display of the finger position presentation image in the wristband-type device illustrated in FIG. 4.

FIG. 9 is a diagram illustrating exemplary display of the finger position presentation image 71 in the wristband-type device 51 illustrated in FIG. 4.

In FIG. 9, the finger position presentation image 71 is displayed on the display 53 at the position of the detection area 55 of the fingerprint sensor 54 (see FIG. 3) embedded in the display 53. Note that an image of a broken line indicating the detection area 55 is not displayed. Furthermore, as in FIGS. 6A, 6B and 6C, the cross image 72, the fingertip image 73, and the circle mark 75 are superimposed and displayed in a stepwise manner at the start of the fingerprint registration process. The finger position presentation image generation unit 66 of FIG. 5 generates the finger position presentation image 71 to be displayed on the display 42 in this manner, and supplies it to the image output unit 24.

In the display of the finger position presentation image 71 described above, the finger position presentation image generation unit 66 may generate the finger position presentation image 71 in FIG. 6C including the cross image 72, the fingertip image 73, and the circle mark 75 to cause the display unit 15 (displays 42 and 53) to display it without generating the finger position presentation images 71 in FIGS. 6A and 6B.

Furthermore, the finger position presentation image generation unit 66 may generate an image including any one or two of the cross image 72, the fingertip image 73, and the circle mark 75 as the finger position presentation image 71 to cause the display unit 15 to display it. Only the cross image 72 may be displayed by informing that the nail root of the user is to be aligned with the position of the finger position reference point 72C of the cross image 72 to the user. Only the fingertip image 73 may be displayed by informing that the finger root of the user is to be aligned with the position of the nail root 74A (FIGS. 6A, 6B and 6C) of the fingertip image 73 to the user. Only the circle mark 75 may be displayed by informing that the nail root of the user is to be aligned with the position of the circle mark 75 to the user.

Furthermore, as in FIGS. 6A, 6B and 6C, the cross image 72, the fingertip image 73, and the circle mark 75 may be superimposed and displayed in a stepwise manner not only at the start of the fingerprint registration process but also in a case of changing and redisplaying the display position of the finger position presentation image 71, that is, in a case of changing and redisplaying the finger position presented by the finger position presentation image 71.

Furthermore, the fingertip image 73 may be an image of only the nail image 74 (an image without the outline of the fingertip).

Figure 10:
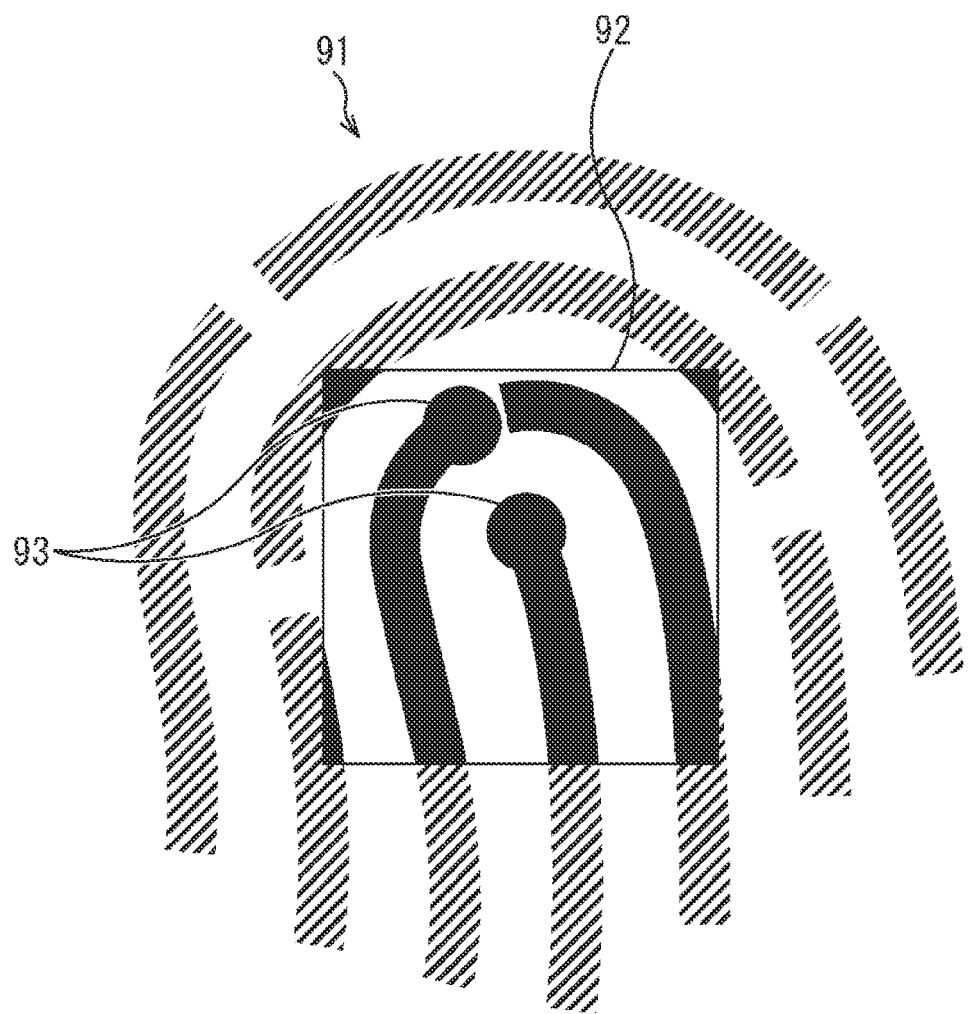
FIG. 10 is a diagram exemplifying a fingerprint image obtained by the fingerprint sensor when a user touches a first finger position presented by the finger position presentation image with a finger.

FIG. 10 is a diagram exemplifying a fingerprint image obtained by the fingerprint sensor 12 in a case where the user touches the first finger position presented by the finger position presentation image 71 with a finger.

In FIG. 10, a fingerprint 91 is a diagram illustrating the fingerprint of the user in a simplified manner. A fingerprint image 92 indicates a fingerprint image obtained by the fingerprint sensor 12 when the user touches the first finger position presented by the finger position presentation image 71 of FIGS. 6A, 6B and 6C with a finger. Furthermore, the fingerprint image 92 represents a fingerprint image obtained from a contact portion of the fingerprint 91 with respect to the detection area 12A of the fingerprint sensor 12. The fingerprint image 92 obtained by the fingerprint sensor 12 is captured by the fingerprint image capturing unit 61 of FIG. 5, and then supplied to the feature amount detection unit 62.

The feature amount detection unit 62 extracts a feature point 93 (minutia) exemplified in FIG. 10 from the fingerprint image 92, and calculates a feature amount of the extracted feature point 93. The feature point 93 is, for example, an end point or branching point of a ridge of the fingerprint 91, and the feature amount is a value indicating the position and direction of the feature point 93.

Figure 11:
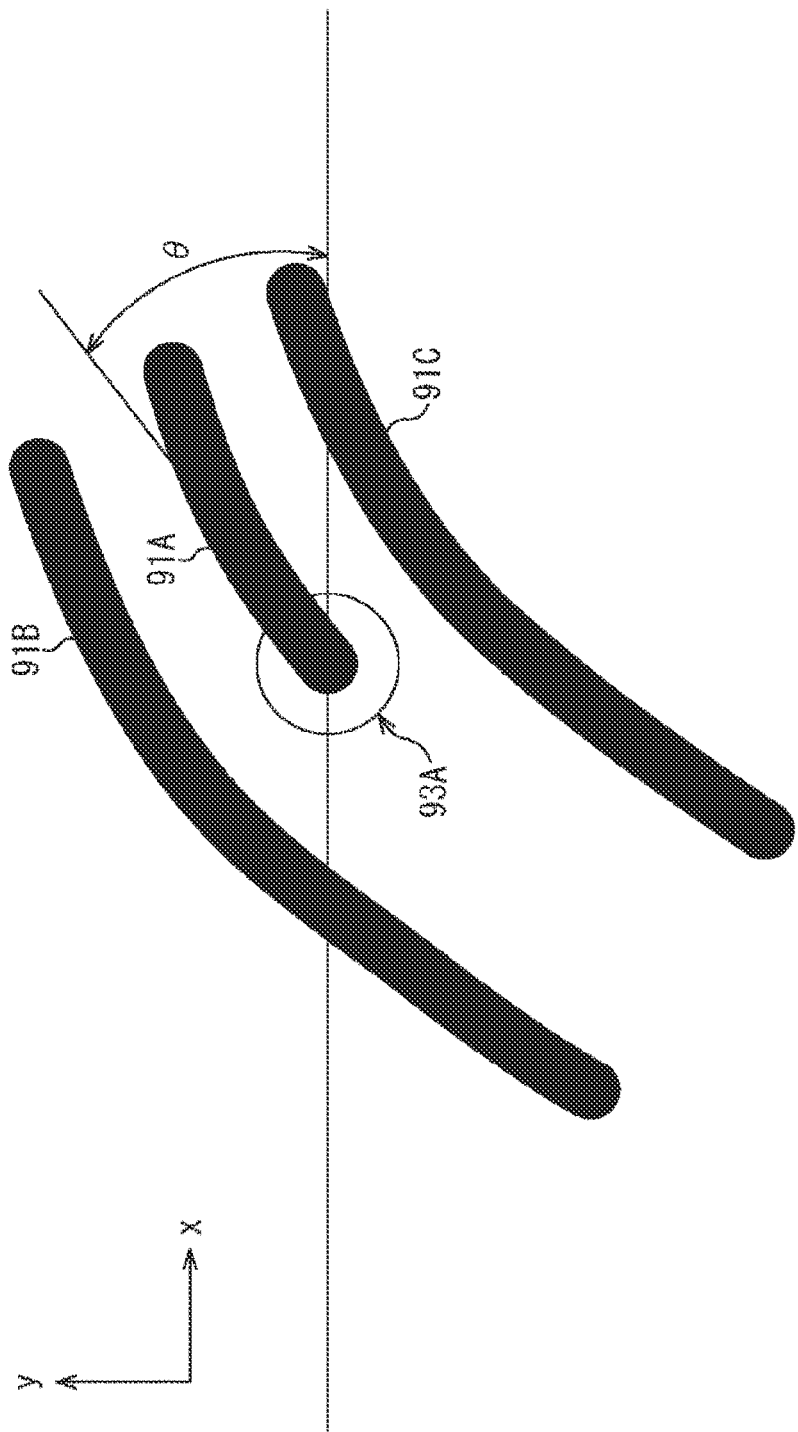
FIG. 11 is an enlarged view exemplifying end points of fingerprint ridges.

FIG. 11 is an enlarged view exemplifying end points of ridges of the fingerprint 91. In FIG. 11, ridges 91A, 91B, and 91C indicate portions where the skin is raised, and an end point 93A indicates a portion where the protuberance of the ridge 91A ends. The feature amount detection unit 62 of FIG. 5 extracts the end point 93A in the fingerprint image 92 as the feature point 93. Then, the feature amount detection unit 62 obtains an xy coordinate value (x, y) of the xy coordinate system as a position of the end point 93A. Note that the x-axis of the xy coordinate system is a coordinate axis in the horizontal direction of the fingerprint image 92, and the y-axis of the xy coordinate system is a coordinate axis in the vertical direction of the fingerprint image 92. Furthermore, the feature amount detection unit 62 obtains an angle θ formed by the axis at the end point 93A of the ridge 91A with the x-axis. Then, the feature amount detection unit 62 sets a value (x, y, θ) including the xy coordinate value (x, y) of the end point 93A and the angle θ as a feature amount (x, y, θ) representing the position and direction of the feature point 93.

Figure 12:
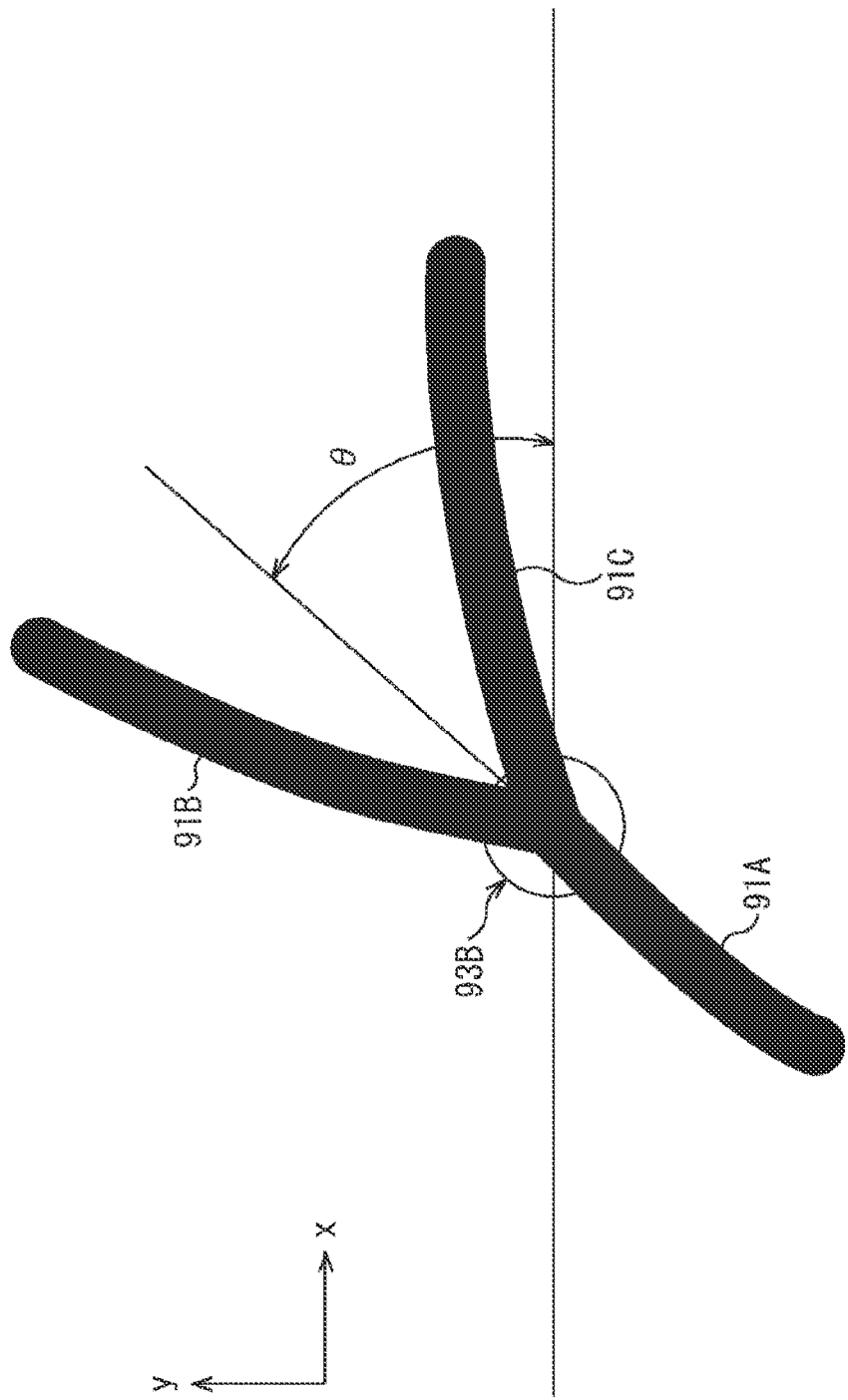
FIG. 12 is an enlarged view exemplifying a branching point of fingerprint ridges.

Furthermore, FIG. 12 is an enlarged view exemplifying a branching point of the ridges of the fingerprint 91. In FIG. 12, the ridges 91A, 91B, and 91C are portions where the skin is raised, and a branching point 93B indicates a portion where the ridge 91A branches into ridges 91B and 91C. The feature amount detection unit 62 of FIG. 5 extracts the branching point 93B in the fingerprint image 92 as the feature point 93. Then, the feature amount detection unit 62 obtains an xy coordinate value (x, y) of the xy coordinate system as a position of the branching point 93B. Furthermore, the feature amount detection unit 62 obtains an angle θ formed by the axis at the branching point 93B of the ridge 91A with the x-axis. Then, the feature amount detection unit 62 sets a value (x, y, θ) including the xy coordinate value (x, y) of the branching point 93B and the angle θ as a feature amount (x, y, θ) representing the position and direction of the feature point 93.

In FIG. 5, the feature amount detection unit 62 supplies the feature amount (x, y, θ) obtained by extracting each feature point 93 from the fingerprint image 92 to the collation unit 63.

The collation unit 63 collates the feature amount from the feature amount detection unit 62 with the feature amount registered as a template. Then, the collation unit 63 registers a feature amount not registered as a template among the feature amounts from the feature amount detection unit 62 as a template. Note that none the feature amounts initially supplied from the feature amount detection unit 62 after the start of the fingerprint registration process is registered as a template, and thus all the feature amounts are registered as a template.

Furthermore, the finger position presented by the finger position presentation image 71 displayed on the display unit 15 is not changed until a predetermined condition (to be described later) is satisfied, and the user continues a state of touching the same position with the finger. While the user continues that state, a fingerprint image 92 at substantially the same position of the fingerprint 91 are repeatedly captured from the fingerprint sensor 12 to the fingerprint image capturing unit 61. Then, a feature amount detected from the fingerprint image 92 at substantially the same position is repeatedly supplied from the feature amount detection unit 62 to the collation unit 63.

Each time the feature amount is supplied from the feature amount detection unit 62, the collation unit 63 collates the feature amount from the feature amount detection unit 62 with the feature amount registered in the template. Then, the collation unit 63 determines that the collation is matched in a case where a degree of matching between the feature amount from the feature amount detection unit 62 and the feature amount registered in the template is equal to or higher than a predetermined threshold value, and determines that the collation is not matched in a case of less than the threshold value. The collation unit 63 supplies a collation result as to whether the feature amount from the feature amount detection unit 62 and the feature amount registered in the template match with each other to the centralized processing unit 64.

Furthermore, the collation unit 63 estimates a correspondence relationship between the feature amount detected by the feature amount detection unit 62 and the feature amount registered in the template from a positional relationship between the feature amounts (feature points) detected by the feature amount detection unit 62 and a positional relationship between the feature amounts (feature points) registered in the template. That is, the collation unit 63 associates the feature amounts of the same feature point with the feature amounts detected by the feature amount detection unit 62 and the feature amounts registered in the template. Then, the collation unit 63 corrects a positional displacement and a rotational displacement of all the feature amounts (x, y, θ) detected at one time by the feature amount detection unit 62 by a parallel translation and a rotational transfer of the xy coordinate system in such a manner that the associated feature amounts (x, y, θ) of the same feature point have the same value.

Note that, in FIG. 5, the fingerprint image obtained by the fingerprint sensor 12 is supplied from the fingerprint image capturing unit 61 to the fingerprint image combining unit 65. The fingerprint image combining unit 65 synthesizes (combines) the fingerprint images supplied from the fingerprint image capturing unit 61, and generates a combined image of the entire range of the fingerprint from which the fingerprint image has been obtained by the fingerprint sensor 12. Then, the fingerprint image combining unit 65 performs a matching process (e.g., a process using a method of phase only correlation) at the time of combining the fingerprint images from the fingerprint image capturing unit 61 into a combined image, and detects and corrects a positional displacement and a rotational displacement of the fingerprint image from the fingerprint image capturing unit 61 with respect to the combined image. The collation unit 63 may correct the positional displacement and rotational displacement of the feature amount from the feature amount detection unit 62 by obtaining information regarding the positional displacement and rotational displacement from the fingerprint image combining unit 65.

Each time a collation result is supplied from the collation unit 63, the centralized processing unit 64 causes the fingerprint image capturing unit 61 to capture a fingerprint image. Then, the centralized processing unit 64 determines whether or not the collation result from the collation unit 63 is matched N times (N is a predetermined positive integer) in succession. Here, in a case where the collation result from the collation unit 63 is matched N times in succession, it can be considered that there is substantially no feature amount to be newly registered as a template in the fingerprint image 92 repeatedly captured by the fingerprint image capturing unit 61 from the fingerprint sensor 12. Accordingly, in a case where the collation result from the collation unit 63 is matched N times in succession, the centralized processing unit 64 instructs the finger position presentation image generation unit 66 to change the finger position presented by the finger position presentation image 71.

When the instruction to change the finger position is issued by the centralized processing unit 64, the finger position presentation image generation unit 66 generates the finger position presentation image 71 for presenting a second finger position, and supplies it to the image output unit 24.

Figure 13:
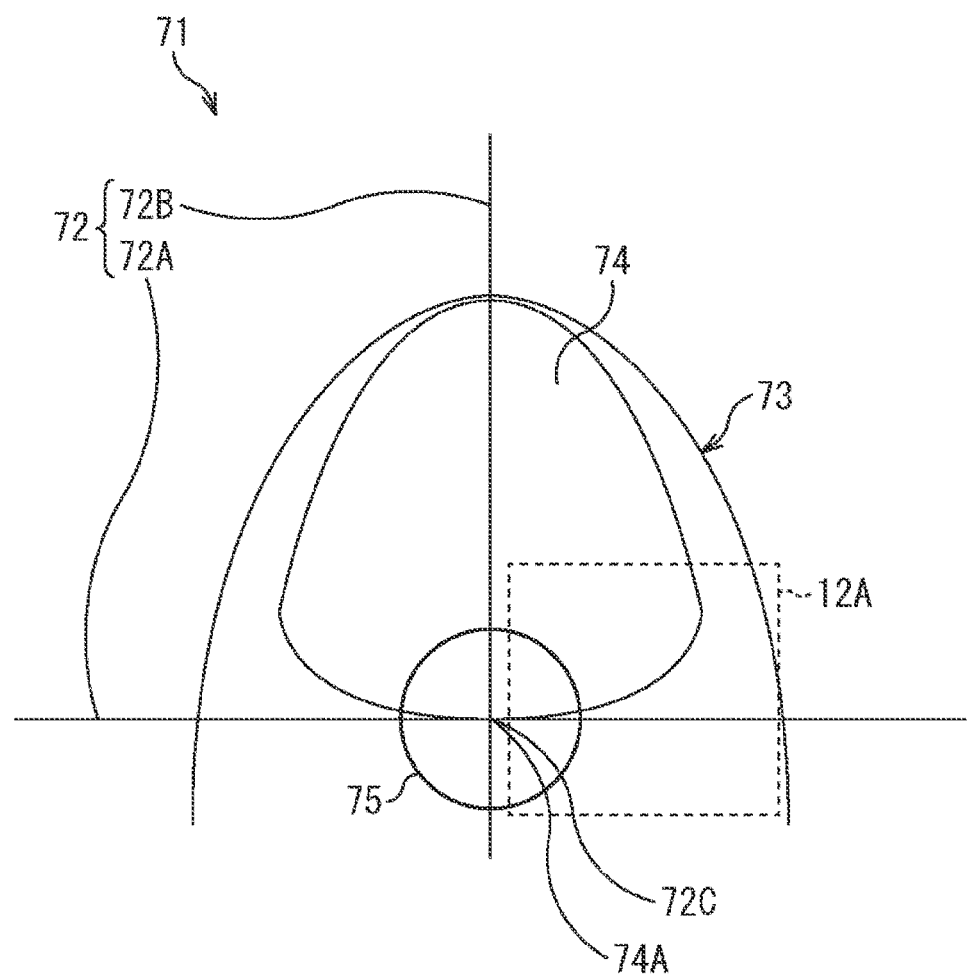
FIG. 13 is a diagram exemplifying the finger position presentation image that presents a second finger position.

FIG. 13 is a diagram exemplifying the finger position presentation image 71 that presents the second finger position. Note that, since the finger position presentation image 71 of FIG. 13 is the same as the finger position presentation image 71 in FIG. 6C, parts corresponding to those of the finger position presentation image 71 in FIG. 6C are denoted by the same reference signs, and descriptions thereof will be omitted.

In FIG. 13, the finger position presented by the finger position presentation image 71 is displaced to the left side as compared with the case of FIGS. 6A, 6B and 6C. That is, while the finger position reference point 72C of the finger position presentation image 71 is displayed at a substantially central position of the detection area 12A of the fingerprint sensor 12 in FIG. 6C, in FIG. 13, the finger position reference point 72C of the finger position presentation image 71 is displayed at a left position outside the detection area 12A.

The user moves the finger from the first finger position presented by the finger position presentation image 71 of FIGS. 6A, 6B and 6C, and touches the position presented by the finger position presentation image 71 of FIG. 13 in such a manner that the nail root is located at the position of the finger position reference point 72C of the finger position presentation image 71 of FIG. 13. Accordingly, the contact portion of the fingerprint with respect to the detection area 12A of the fingerprint sensor 12 is changed.

Figure 14:
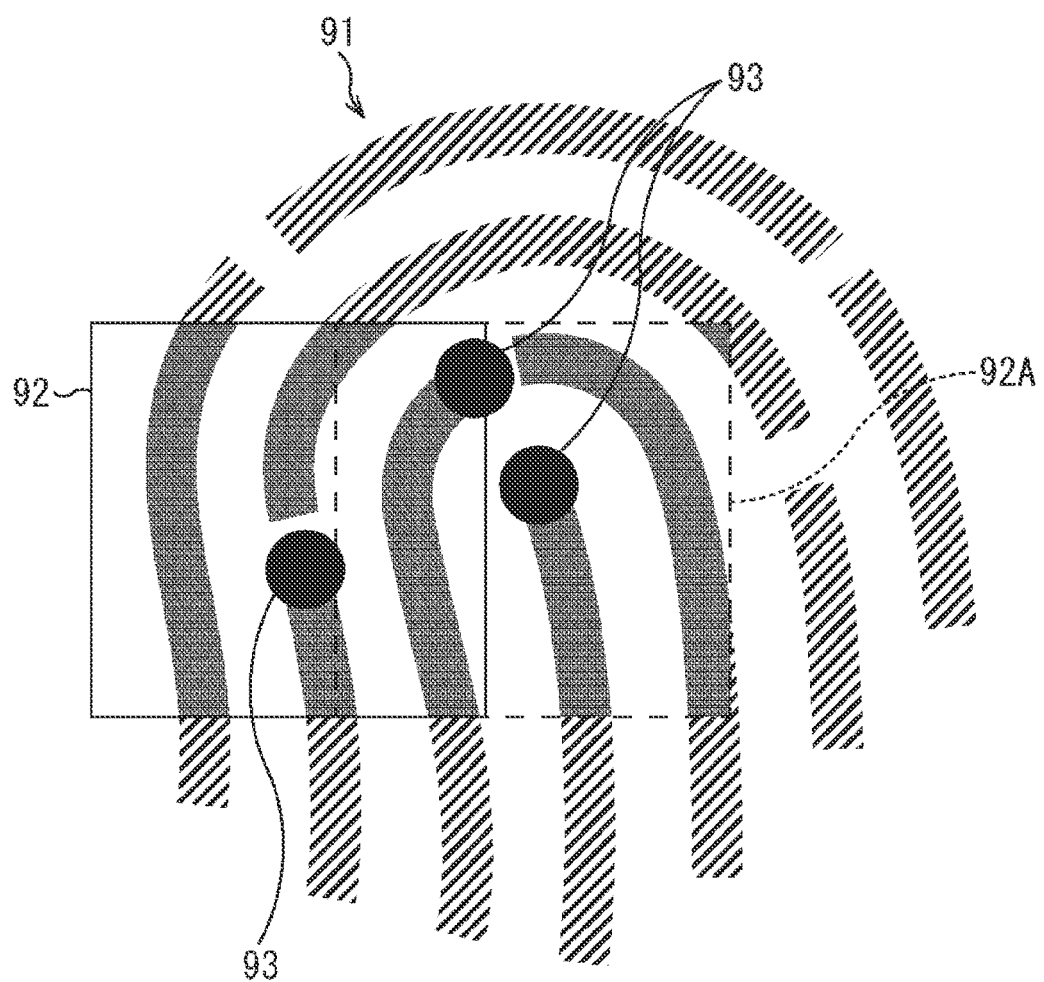
FIG. 14 is a diagram exemplifying a fingerprint image obtained by the fingerprint sensor when the user touches the second finger position presented by the finger position presentation image of FIG. 13 with a finger.

FIG. 14 is a diagram exemplifying a fingerprint image obtained by the fingerprint sensor 12 in a case where the user touches the second finger position presented by the finger position presentation image 71 of FIG. 13 with a finger.

In FIG. 14, the fingerprint 91 is a diagram illustrating the fingerprint of the user in a simplified manner. The fingerprint image 92 indicates a fingerprint image obtained by the fingerprint sensor 12 when the user touches the finger position presented by the finger position presentation image 71 of FIG. 13 with a finger. Furthermore, the fingerprint image 92 represents a fingerprint image obtained from a contact portion of the fingerprint 91 with respect to the detection area 12A of the fingerprint sensor 12. A captured fingerprint image 92A indicated by a broken line indicates the fingerprint image already captured by the fingerprint sensor 12, which is the fingerprint image captured when the first finger position presented by the finger position presentation image 71 of FIGS. 6A, 6B and 6C is touched with the finger.

With the finger position presented by the finger position presentation image 71 displaced to the left side as compared with the case of FIGS. 6A, 6B and 6C as illustrated in FIG. 13, the contact portion of the fingerprint 91 with respect to the detection area 12A is displaced to the left side in a case where the finger is viewed from the side of the fingerprint. As a result, in FIG. 14, the fingerprint image 92 is obtained from the range on the left side of the fingerprint 91 as compared with the fingerprint image 92A. Furthermore, a fingerprint image in a partial range of the fingerprint image 92 overlaps with a fingerprint image in a partial range of the fingerprint image 92A.

Figure 15B:
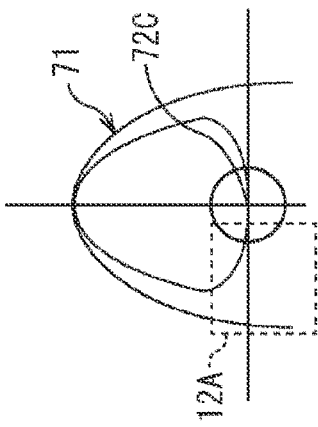
FIGS. 15A, 15B, 15C, 15D and 15E are diagrams for explaining a correspondence relationship between the finger position presented by the finger position presentation image and the position of the fingerprint image obtained by the fingerprint sensor in a case where the position presented by the finger position presentation image is touched by a finger, which is a diagram illustrating the finger position presented by the finger position presentation image.
Figure 15D:
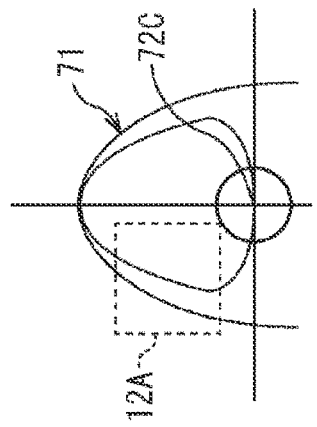
Figure 15A:
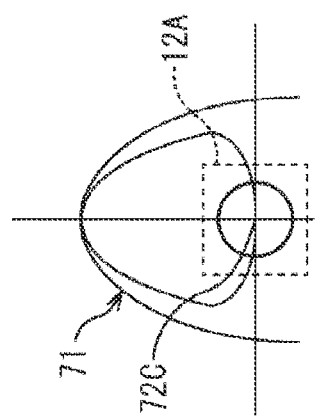
Figure 15C:
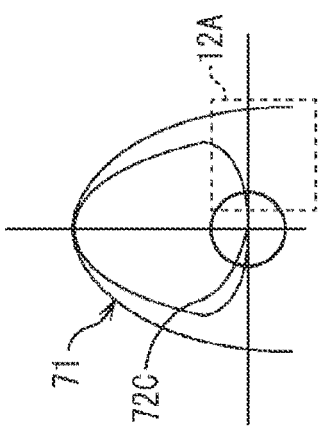
Figure 15E:
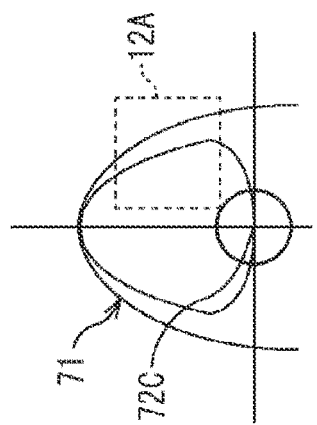
Figure 16C:
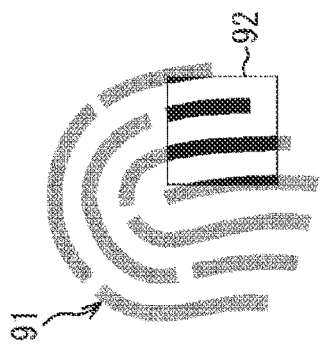
FIGS. 16A, 16B, 16C, 16D and 16E are diagrams for explaining the correspondence relationship between the finger position presented by the finger position presentation image and the position of the fingerprint image obtained by the fingerprint sensor in a case where the position presented by the finger position presentation image is touched by a finger, which is a diagram illustrating the position of the fingerprint image obtained by the fingerprint sensor.
Figure 16E:
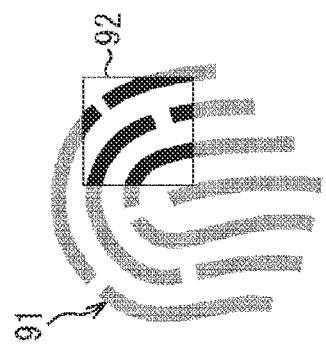
Figure 16A:
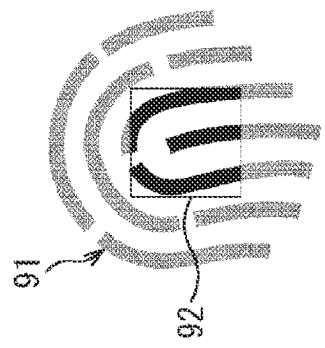
Figure 16B:
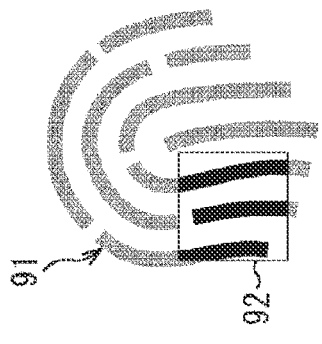

Here, FIGS. 15A, 15B, 15C, 15D, 15E, 16A, 16B, 16C, 16D and 16E are diagrams illustrating a correspondence relationship between the finger position presented by the finger position presentation image 71 and the position of the fingerprint image obtained by the fingerprint sensor 12 in a case where the position presented by the finger position presentation image 71 is touched by the finger. FIG. 15A illustrates a case where the finger position presentation image 71 is displayed in such a manner that the finger position reference point 72C of the finger position presentation image 71 is at a substantially central position of the detection area 12A of the fingerprint sensor 12. FIG. 16B illustrates a position of the fingerprint image 92 obtained by the fingerprint sensor 12 in a case where the position presented by the finger position presentation image 71 in FIG. 15A is touched with a finger. In FIG. 16A, the fingerprint image 92 is obtained from a substantially central range of the fingerprint 91.

FIG. 15B illustrates a case where the finger position presentation image 71 is displayed in such a manner that the finger position reference point 72C of the finger position presentation image 71 is at a diagonally upper left position with respect to the central position of the detection area 12A of the fingerprint sensor 12. FIG. 16B illustrates a position of the fingerprint image 92 obtained by the fingerprint sensor 12 in a case where the position presented by the finger position presentation image 71 in FIG. 15B is touched with a finger. In FIG. 16B, the fingerprint image 92 is obtained from a range diagonally lower left of the central range of the fingerprint 91.

FIG. 15C illustrates a case where the finger position presentation image 71 is displayed in such a manner that the finger position reference point 72C of the finger position presentation image 71 is at a diagonally upper right position with respect to the central position of the detection area 12A of the fingerprint sensor 12. FIG. 16C illustrates a position of the fingerprint image 92 obtained by the fingerprint sensor 12 in a case where the position presented by the finger position presentation image 71 in FIG. 15C is touched with a finger. In FIG. 16C, the fingerprint image 92 is obtained from a range diagonally lower right of a substantially central range of the fingerprint 91.

Figure 16D:
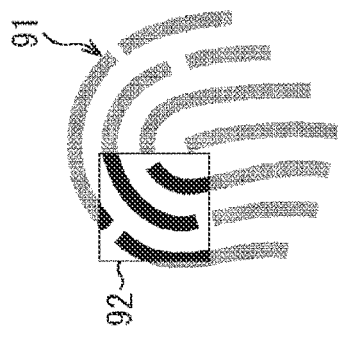

FIG. 15D illustrates a case where the finger position presentation image 71 is displayed in such a manner that the finger position reference point 72C of the finger position presentation image 71 is at a diagonally lower left position with respect to the central position of the detection area 12A of the fingerprint sensor 12. FIG. 16D illustrates a position of the fingerprint image 92 obtained by the fingerprint sensor 12 in a case where the position presented by the finger position presentation image 71 in FIG. 15D is touched with a finger. In FIG. 16D, the fingerprint image 92 is obtained from a range diagonally upper left of the central range of the fingerprint 91.

FIG. 15E illustrates a case where the finger position presentation image 71 is displayed in such a manner that the finger position reference point 72C of the finger position presentation image 71 is at a diagonally lower right position with respect to the central position of the detection area 12A of the fingerprint sensor 12. FIG. 16E illustrates a position of the fingerprint image 92 obtained by the fingerprint sensor 12 in a case where the position presented by the finger position presentation image 71 in FIG. 15E is touched with a finger. In FIG. 16E, the fingerprint image 92 is obtained from a range diagonally upper right of the central range of the fingerprint 91.

The fingerprint image 92 of FIG. 14 obtained by the fingerprint sensor 12 is captured by the fingerprint image capturing unit 61, and then supplied to the feature amount detection unit 62. Then, the fingerprint registration processing unit 22 of FIG. 5 performs a process similar to that in the case where the first finger position is presented by the finger position presentation image 71 (description is omitted).

In a case where the collation result from the collation unit 63 is matched N times in succession, the centralized processing unit 64 instructs the finger position presentation image generation unit 66 to change the finger position presented by the finger position presentation image 71.

When the instruction to change the finger position is issued by the centralized processing unit 64, the finger position presentation image generation unit 66 generates the finger position presentation image 71 for presenting a third finger position, and supplies it to the image output unit 24.

Figure 17:
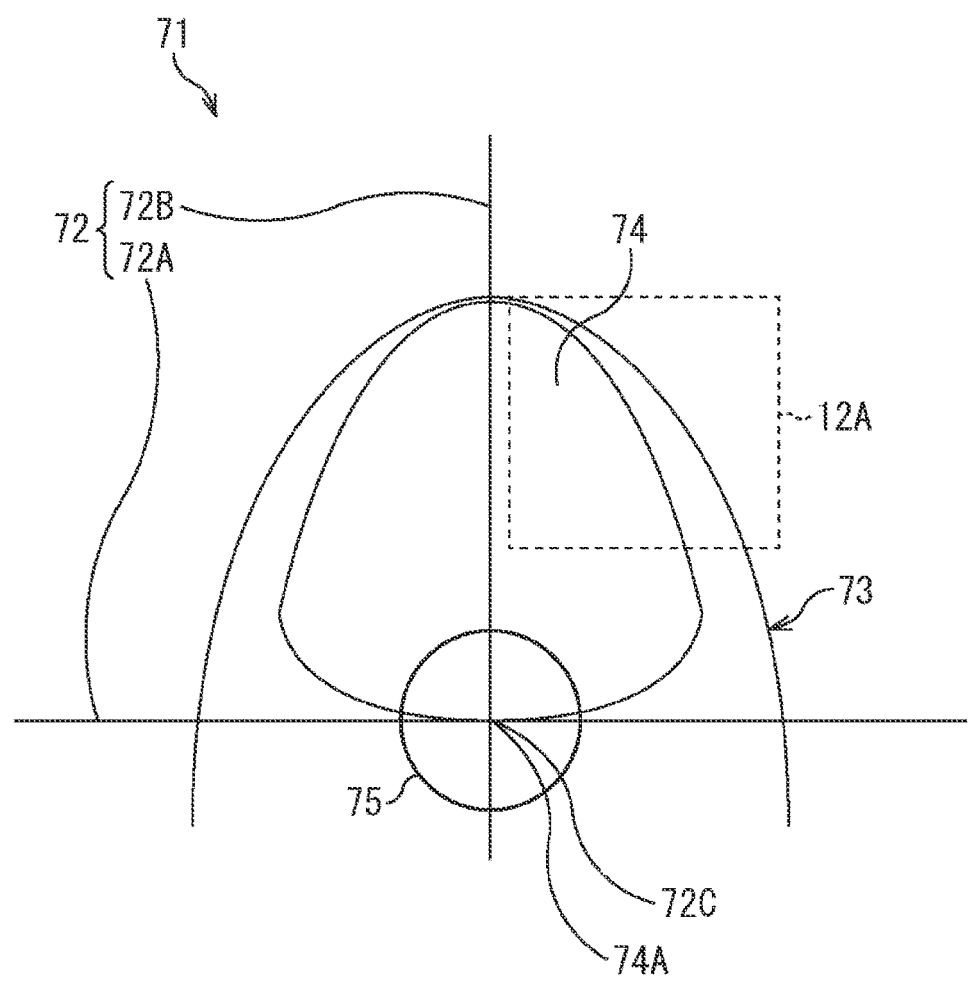
FIG. 17 is a diagram exemplifying the finger position presentation image that presents a third finger position.

FIG. 17 is a diagram exemplifying the finger position presentation image 71 that presents the third finger position. Note that, since the finger position presentation image 71 of FIG. 17 is the same as the finger position presentation image 71 in FIG. 6C, parts corresponding to those of the finger position presentation image 71 in FIG. 6C are denoted by the same reference signs, and descriptions thereof will be omitted.

In FIG. 17, the finger position presented by the finger position presentation image 71 is displaced to the lower side as compared with the case of FIG. 13.

The user moves the finger from the second position presented by the finger position presentation image 71 of FIG. 13, and touches the third finger position presented by the finger position presentation image 71 of FIG. 17 in such a manner that the nail root is located at the position of the finger position reference point 72C of the finger position presentation image 71 of FIG. 17. Accordingly, the contact portion of the fingerprint with respect to the detection area 12A of the fingerprint sensor 12 is changed as compared with the cases of FIGS. 6A, 6B, 6C and 13

Figure 18:
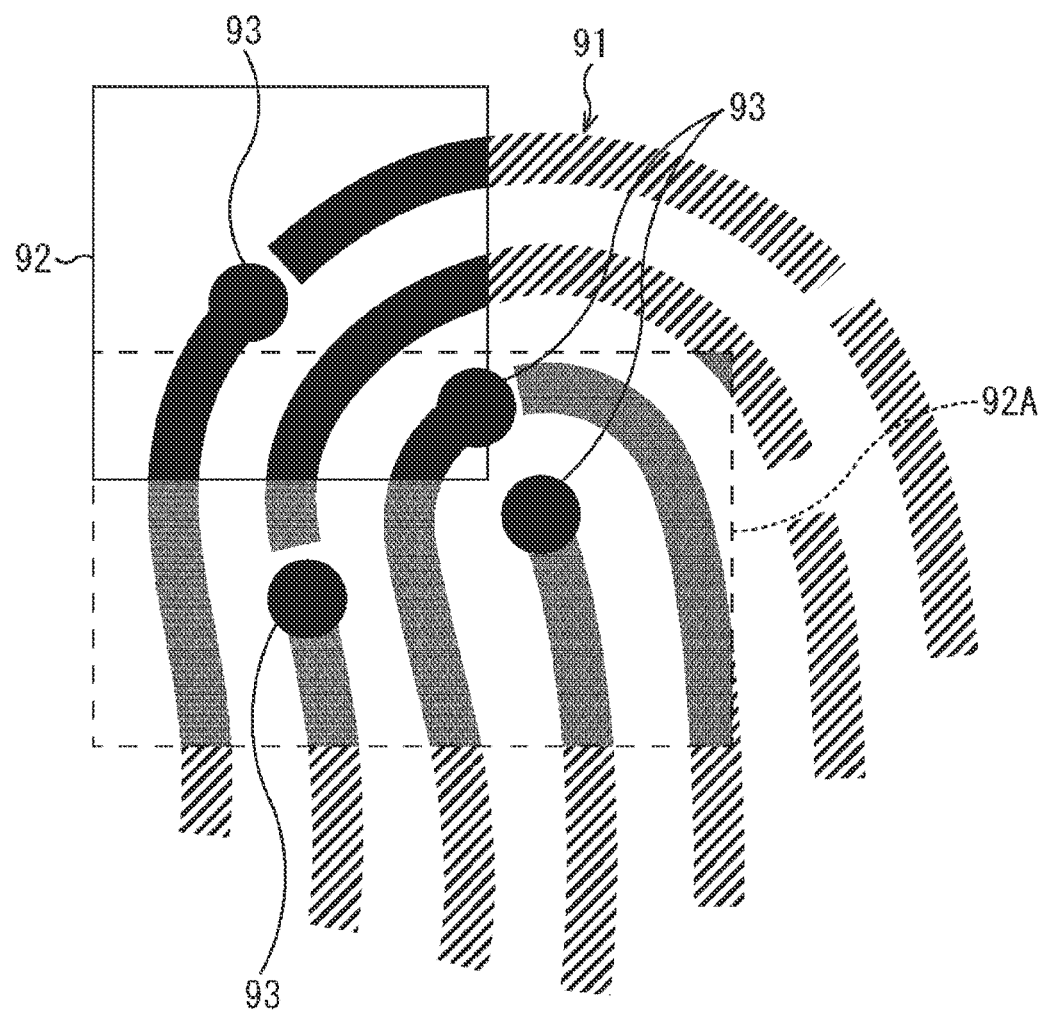
FIG. 18 is a diagram exemplifying a fingerprint image obtained by the fingerprint sensor when the user touches the third position presented by the finger position presentation image of FIG. 17 with a finger.

FIG. 18 is a diagram exemplifying a fingerprint image obtained by the fingerprint sensor 12 in a case where the user touches the third position presented by the finger position presentation image of FIG. 17 with a finger.

In FIG. 18, the fingerprint 91 is a diagram illustrating the fingerprint of the user in a simplified manner. The fingerprint image 92 indicates a fingerprint image obtained by the fingerprint sensor 12 when the user touches the third finger position presented by the finger position presentation image 71 of FIG. 17 with a finger. Furthermore, the fingerprint image 92 represents a fingerprint image obtained from a contact portion of the fingerprint 91 with respect to the detection area 12A of the fingerprint sensor 12. The captured fingerprint image 92A indicated by a broken line indicates the fingerprint image already captured by the fingerprint sensor 12, which is the fingerprint image captured when the user touches the first and second finger positions presented by the finger position presentation image 71 of FIGS. 6A, 6B, 6C and 13 with the finger.

With the finger position presented by the finger position presentation image 71 displaced to the lower side as compared with the case of FIG. 13 as illustrated in FIG. 17, the contact portion of the fingerprint 91 with respect to the detection area 12A is displaced to the upper side in a case where the finger is viewed from the side of the fingerprint. As a result, in FIG. 18, the fingerprint image 92 is obtained from the range on the upper left side of the fingerprint 91 as compared with the fingerprint image 92A.

Furthermore, a fingerprint image in a partial range of the fingerprint image 92 overlaps with a fingerprint image in a partial range of the fingerprint image 92A.

The fingerprint image 92 of FIG. 18 obtained by the fingerprint sensor 12 is captured by the fingerprint image capturing unit 61, and then supplied to the feature amount detection unit 62. Then, the fingerprint registration processing unit 22 of FIG. 5 performs a process similar to that in the case where the first and second finger positions are presented by the finger position presentation image 71 (description is omitted).

In a case where the collation result from the collation unit 63 is matched N times in succession, the centralized processing unit 64 instructs the finger position presentation image generation unit 66 to change the finger position presented to the user by the finger position presentation image 71.

When the instruction to change the finger position is issued by the centralized processing unit 64, the finger position presentation image generation unit 66 generates the finger position presentation image 71 for presenting a fourth finger position, and supplies it to the image output unit 24.

Figure 19:
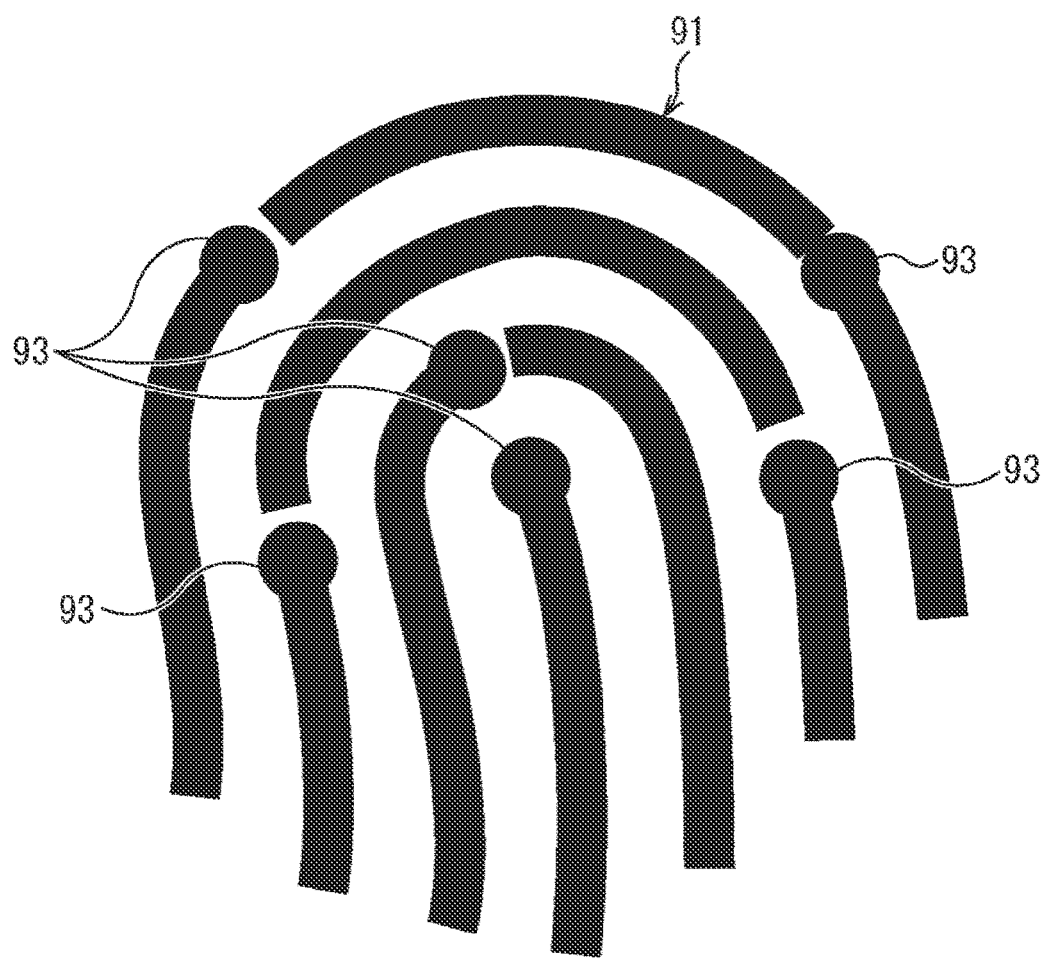
FIG. 19 is a diagram illustrating a state where a fingerprint image and feature amount of the entire fingerprint range are obtained.

As described above, the finger position presentation image generation unit 66 sequentially changes the finger position to be presented by the finger position presentation image 71 to the predetermined first to M-th finger positions so that the contact portion of the fingerprint with respect to the detection area 12A of the fingerprint sensor 12 extends over the entire range of the fingerprint. With this arrangement, the fingerprint image of the entire range of the fingerprint 91 is obtained as illustrated in FIG. 19. Furthermore, the feature points 93 in the entire range of the fingerprint are detected by the feature amount detection unit 62, and registered as a template of the storage unit 14 to be used for fingerprint authentication. Note that, in a case where, for example, the user touches a position different from the finger position presented by the finger position presentation image 71, there may be a missing portion where the fingerprint image and the feature amount are not obtained in a partial range of the fingerprint. In that case, the finger position presentation image 71 may be displayed at a position where a fingerprint image of the missing portion can be obtained to obtain the fingerprint image and the feature amount of the missing portion.

According to the finger position presentation using the finger position presentation image 71 in FIGS. 6A, 6B, 6C, 13, 17, and the like described above, the user is enabled to easily and accurately touch the finger position presented by the finger position presentation image 71, thereby facilitating acquisition of fingerprint information (feature amount) in the intended range of the fingerprint. Therefore, in a case where the fingerprint sensor 12 is a small-area sensor, the time required to register the fingerprint and the number of times of touching by changing the finger position are reduced, and registration of the fingerprint (fingerprint information) is performed efficiently. According to the technique of Japanese Patent Application Laid-Open No. 2018-195316, it is difficult to specify a touch position with high reproducibility as in the present technology, and it is difficult to reduce the number of times of touching in a case where the fingerprint sensor 12 is a small-area sensor.

<Acquisition Status Image>

Next, an acquisition status image that presents an acquisition status of a feature amount will be described.

After the display unit 15 displays the finger position presentation image 71 that presents the m-th (m is a positive integer) finger position, the centralized processing unit 64 in FIG. 5 counts the number of feature amounts (feature points) detected by the feature amount detection unit 62 before the display unit 15 displays the finger position presentation image 71 that presents the next (m+1)-th finger position. Then, the centralized processing unit 64 obtains a progress rate (hereinafter referred to as a progress rate of feature amount acquisition) of the feature amount detection on the basis of a counted number d of the feature amounts, and supplies it to the acquisition status image generation unit 67. For example, the centralized processing unit 64 sets the number of feature amounts for which the progress rate is 100% as a comparison value D, and calculates a progress rate (d/D)×100 (percent) of the feature amount acquisition from the counted number d of the feature amounts and the comparison value D. The comparison value D is determined in advance on the basis of the general number of feature amounts detected from a fingerprint in the range having the size of the detection area 12A of the fingerprint sensor 12. Furthermore, in a case where the counted number d of the feature amounts is larger than the comparison value D, the progress rate of the feature amount acquisition is set to 100%.

Note that the progress rate of the feature amount acquisition may be a value calculated on the basis of the density of the detected feature amounts (feature points).

The acquisition status image generation unit 67 generates an acquisition status image that presents the acquisition status of the feature amount to the user on the basis of the progress rate of the feature amount acquisition from the centralized processing unit 64, and supplies it to the image output unit 24. With this arrangement, the acquisition status image generated by the acquisition status image generation unit 67 is displayed on the display unit 15.

Figure 20:
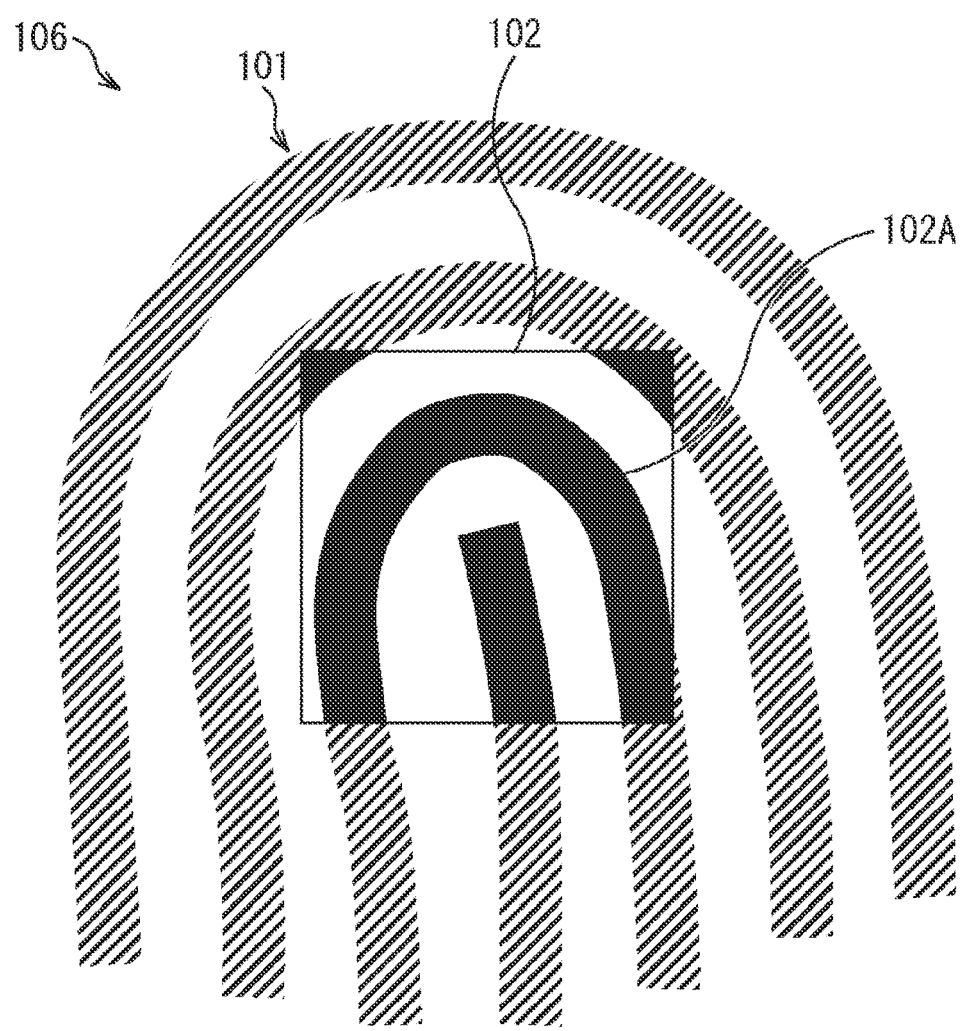
FIG. 20 is a diagram exemplifying a first mode of an acquisition status image that presents an acquisition status of the feature amount.

FIG. 20 is a diagram exemplifying a first mode of the acquisition status image that presents the acquisition status of the feature amount. In FIG. 20, an acquisition status image 106 includes a fingerprint image 101, and a fingerprint image 102A in an indicator area 102.

The fingerprint image 101 is an image imitating a fingerprint, and in a case where the progress rate of the feature amount acquisition is 0%, the entire image is uniformly displayed on the display unit 15 as an image with low density.

The fingerprint image 102A in the indicator area 102 is displayed with density corresponding to the progress rate of the feature amount acquisition, and is displayed as an image with density that increases as the progress rate increases. The fingerprint image 102A is displayed at the maximum density when the progress rate is 100%. The density of the fingerprint image 101 in an area other than the indicator area 102 is displayed as an image with a constant lower density regardless of the progress rate of the feature amount acquisition.

Note that it is sufficient if sharpness of the image is changed according to the progress rate, and a degree of blurring processing, a degree of mosaic processing, brightness, luminance, saturation, or the like may be changed in addition to the change of the image density.

Furthermore, the position of the indicator area 102 in the fingerprint image 101 represents the position of the fingerprint image obtained by the fingerprint sensor 12 within the entire range of the fingerprint. With this arrangement, the user is enabled to recognize the position at which the acquisition of the feature amount (fingerprint information) is performed.

Note that the acquisition status image generation unit 67 in FIG. 5 may obtain and generate the fingerprint image actually obtained by the fingerprint sensor 12 from the fingerprint image combining unit 65 in FIG. 5 instead of the fingerprint images 101 and 102A.

According to the acquisition status image 106 of FIG. 20, the user is enabled to grasp the acquisition status of the feature amount so that the shift (change of the touch position) of the position at which the feature amount is obtained can be performed smoothly, whereby the time required to register the fingerprint can be reduced. Furthermore, the user is enabled to intuitively grasp in which part of the fingerprint range the feature amount has not been obtained, and the position to be touched is changed efficiently. Furthermore, with the acquisition status of the feature amount fed back to the user in real time, it becomes possible to accurately present the presence/absence of the feature amount acquisition to the user, and to prompt the user to improve the way of touching. According to the technique of Japanese Patent Application Laid-Open No. 2018-195316, it is not possible to intuitively grasp a part where the feature amount is not obtained, and it is difficult to efficiently change the position to be touched.

Figure 21B:
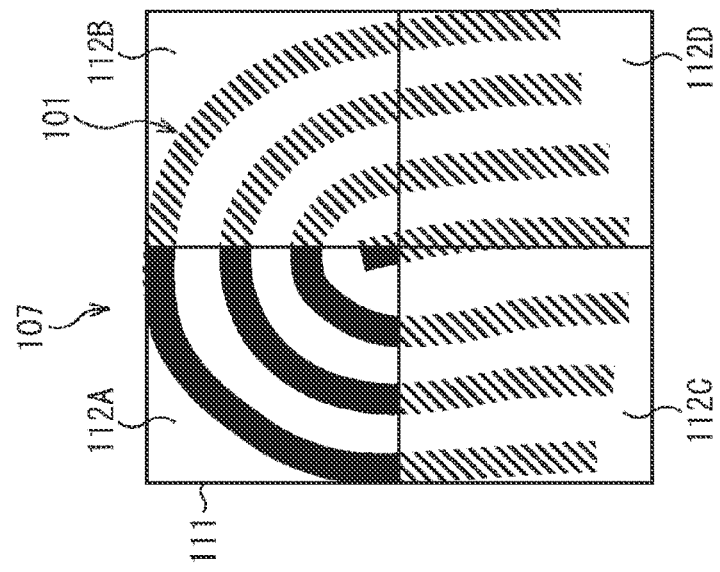
FIGS. 21A and 21B are diagrams exemplifying a second mode of the acquisition status image that presents an acquisition status of the feature amount.
Figure 21A:
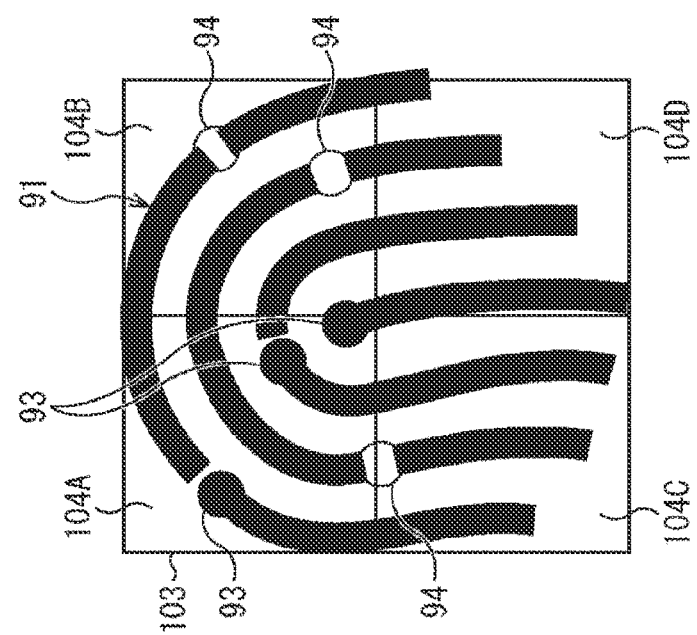

FIGS. 21A and 21B are diagrams exemplifying a second mode of the acquisition status image that presents the acquisition status of the feature amount. In FIG. 21A, the fingerprint 91 is a diagram illustrating the fingerprint of the user in a simplified manner. The feature point 93 represents a detected (obtained) feature point, and a feature point 94 represents an undetected (unobtained) feature point. A divided frame 103 divides the range of the fingerprint 91 into a plurality of (four) divided areas 104A to 104D. The number of divided areas into which the range of the fingerprint 91 is divided by the divided frame 103 is not limited to four.

An acquisition status image 107 in FIG. 21B is an acquisition status image displayed on the display unit 15. In FIG. 21B, the acquisition status image 107 includes the fingerprint image 101 and a divided frame 110.

The fingerprint image 101 is an image imitating a fingerprint, and in a case where the progress rate of the feature amount acquisition is 0% in the entire range of the fingerprint 91, the entire image is uniformly displayed on the display unit 15 as an image with low density.

A divided frame 111 is a frame image that divides the range of the fingerprint image 101 into a plurality of (four) divided areas 112A to 112D corresponding to the divided frame 103 in FIG. 21A.

The centralized processing unit 64 in FIG. 5 obtains a progress rate of the feature amount acquisition for each of the divided areas 104A to 104D in A of FIG. 21, and supplies it to the acquisition status image generation unit 67. The acquisition status image generation unit 67 generates fingerprint images in the respective divided areas 112A to 112D in the acquisition status image 107 in FIG. 21B as images having the densities corresponding to the progress rates of the feature amount acquisition in the corresponding divided areas 104A to 104D in FIG. 21A.

In the acquisition status image 107 in FIG. 21B, the density of the fingerprint images in the respective divided areas 112A to 112D increases as the progress rate of the feature amount acquisition in the corresponding divided areas 104A to 104D in A of FIG. 21 increases.

In the acquisition status image 107 in FIG. 21B, the progress rate of the feature amount acquisition has reached approximately 100% in the divided area 104A in FIG. 21A corresponding to the divided area 112A, and the fingerprint image in the divided area 112A is displayed as an image with higher density. In the acquisition status image 107 in FIG. 21B, the progress rate of the feature amount acquisition is approximately 0% in the divided areas 104B to 104D in FIG. 21A corresponding to the divided areas 112B to 112D other than the divided area 112A, and the fingerprint images in the divided areas 112B to 112D are displayed as images with lower density.

According to the acquisition status image 107 of FIGS. 21A and 21B, the user is enabled to grasp the acquisition status of the feature amount so that the shift (change of the touch position) of the position at which the feature amount is obtained can be performed smoothly, whereby the time required to register the fingerprint can be reduced. Furthermore, the user is enabled to intuitively grasp in which part of the fingerprint range the feature amount has not been obtained, and the position to be touched is changed efficiently. Furthermore, with the acquisition status of the feature amount fed back to the user in real time, it becomes possible to accurately present the presence/absence of the feature amount acquisition to the user, and to prompt the user to improve the way of touching.

FIGS. 22A, 22B, 22C, 22D and 22E are diagrams exemplifying a third mode of the acquisition status image that presents the acquisition status of the feature amount. In FIGS. 22A, 22B, 22C, 22D and 22E, an acquisition status image 108 includes a base image 121, and at least one of a low-density area 122A or a high-density area 122B.

The base image 121 is any image, and an image of a cat is used as an example.

The low-density area 122A is an image area having density lower than that of the high-density area 122B, and the high-density area 122B is an image area having density higher than that of the low-density area 122A.

When the progress rate of the feature amount acquisition is 0% after the finger position presentation image 71 that presents the m-th finger position is displayed on the display unit 15, the entire range of the base image 121 is in the low-density area 122A as in the acquisition status image 108 in FIG. 22A.

Meanwhile, as the progress rate of the feature amount acquisition increases, the area of the low-density area 122A in the base image 121 decreases and the area of the high-density area 122B increases as in the acquisition status image 108 in FIGS. 22B, 22C, 22D and 22E. The high-density area 122B is enlarged from the central portion to the peripheral portion of the base image 121, for example. The acquisition status image 108 in FIG. 22E illustrates a case where the progress rate of the feature amount acquisition has reached 100%, and the entire range of the base image 121 of the acquisition status image 108 is in the high-density area 122B.

Note that the acquisition status image 108 in FIGS. 22A, 22B, 22C, 22D and 22E may be an image corresponding to the entire range of the fingerprint, and a progress status of the feature amount acquisition may be presented in a corresponding area of the acquisition status image 108 (base image 121) corresponding to each small area of a case where the entire range of the fingerprint is divided into small areas. Any method of changing sharpness of the image may be adopted to present the progress rate of the feature amount acquisition in each corresponding area of the acquisition status image 108, such as increasing image density as the progress rate is higher or decreasing a degree of blurring as the progress rate is higher.

According to the acquisition status image 108 of FIGS. 22A, 22B, 22C, 22D and 22E, the user is enabled to grasp the acquisition status of the feature amount so that the shift (change of the touch position) of the position at which the feature amount is obtained can be performed smoothly, whereby the time required to register the fingerprint can be reduced. Furthermore, the user is enabled to intuitively grasp in which part of the fingerprint range the feature amount has not been obtained, and the position to be touched is changed efficiently. Furthermore, with the acquisition status of the feature amount fed back to the user in real time, it becomes possible to accurately present the presence/absence of the feature amount acquisition to the user, and to prompt the user to improve the way of touching. Furthermore, it is possible to give the user a game feeling that the content of the base image 121 is gradually unveiled as the feature amount acquisition progresses, whereby the inconvenience of the registration can be reduced.

Furthermore, in a case where the feature amount detection unit 62 in FIG. 5 does not appropriately detect the feature amount and the progress rate of the feature amount acquisition does not exceed a predetermined threshold value even after a predetermined time has elapsed, the acquisition status image generation unit 67 may generate an error image for presenting occurrence of an error as an acquisition status image, and may supply it to the image output unit 24 to cause the display unit 15 to display it.

Figure 23:
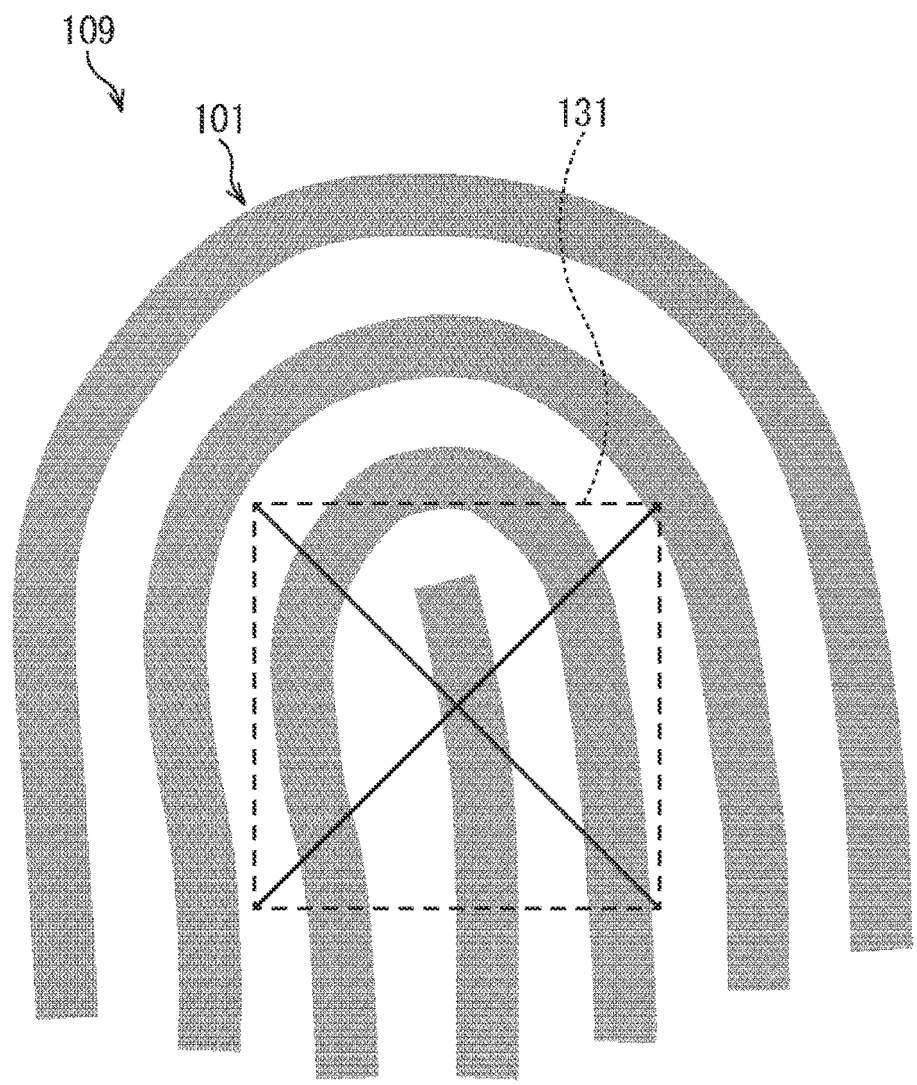
FIG. 23 is a diagram exemplifying an error image that presents an acquisition status of the feature amount.

FIG. 23 is a diagram exemplifying the error image. In FIG. 23, an error image 109 includes the fingerprint image 101 imitating the fingerprint and a framed cross mark 131.

With such an error image 109 displayed on the display unit 15, the user is enabled to visually recognize that the feature amount has not been obtained appropriately.

Furthermore, in a case where an error has occurred, the fingerprint authentication device 11 or a device equipped with the fingerprint authentication device 11 may vibrate without changing the display status of the acquisition status image. Furthermore, in a case where an error has occurred, an image or a character such as the finger position presentation image 71 displayed on the display unit 15 may blink.

<Procedure of Fingerprint Registration Process>

Figure 24:
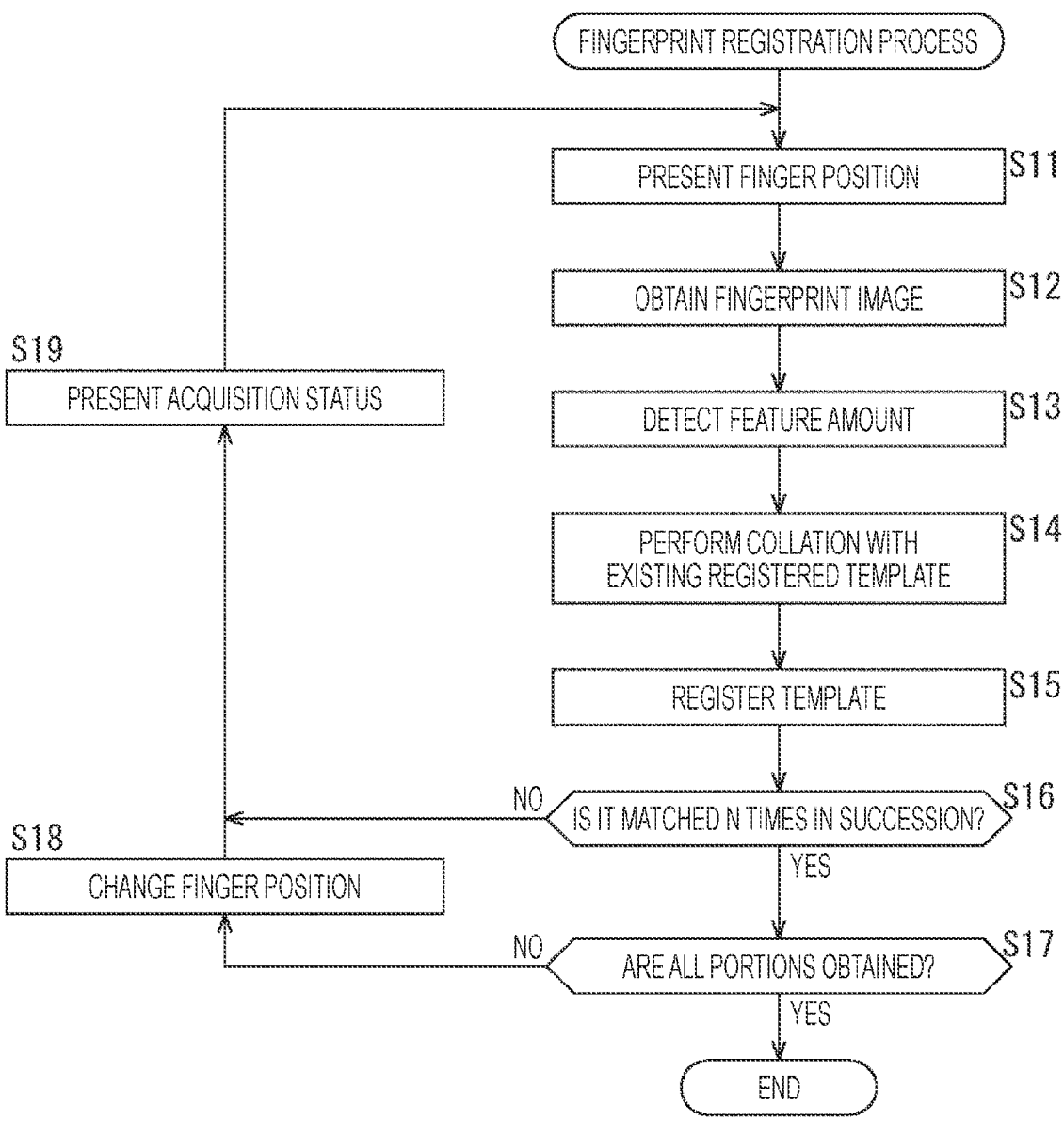
FIG. 24 is a flowchart for explaining an exemplary fingerprint registration process performed by a fingerprint registration processing unit in FIG. 5.

FIG. 24 is a flowchart for explaining an exemplary fingerprint registration process performed by the fingerprint registration processing unit 22 in FIG. 5.

In step S11, the finger position presentation image generation unit 66 generates the finger position presentation image 71 that presents the position to be touched by the user with a finger in the detection area 12A of the fingerprint sensor 12. Then, the finger position presentation image generation unit 66 supplies the generated finger position presentation image 71 to the image output unit 24, and causes the display unit 15 to display it. The process proceeds to step S12 from step S11.

In step S12, the fingerprint image capturing unit 61 obtains a fingerprint image from the fingerprint sensor 12, and supplies it to the feature amount detection unit 62. The process proceeds to step S13 from step S12.

In step S13, the feature amount detection unit 62 extracts feature points from the fingerprint image supplied from the fingerprint image capturing unit 61 in step S12, calculates a feature amount (template) of each feature point, and supplies it to the collation unit 63. The process proceeds to step S14 from step S13.

In step S14, the collation unit 63 collates the feature amount supplied from the feature amount detection unit 62 in step S13 with the feature amount already registered as a template. Then, the collation unit 63 supplies, to the centralized processing unit 64, a collation result as to whether or not the feature amount supplied from the feature amount detection unit 62 and the template match with each other. The process proceeds to step S15 from step S14.

In step S15, the collation unit 63 registers, as a template, a feature amount not registered as a template among the feature amounts supplied from the feature amount detection unit 62 in step S13. The process proceeds to step S16 from step S15.

In step S16, the centralized processing unit 64 determines whether or not the feature amount supplied from the feature amount detection unit 62 matches the template N times in succession on the basis of the collation result supplied from the collation unit 63 in step S14.

In a case where it is not determined to be matched N times in succession in step S16, the process proceeds to step S19.

Furthermore, in a case where it is determined to be matched N times in succession in step S16, the process proceeds to step S17, and the centralized processing unit 64 determines whether or not fingerprint images and feature amounts of the entire range (all portions) of the fingerprint have been obtained. That is, the centralized processing unit 64 determines whether or not the finger position presented by the finger position presentation image in step S11 has been changed to a predetermined M-th finger position.

In a case where the fingerprint images and feature amounts of all portions of the fingerprint are not determined to have been obtained in step S17, that is, in a case where the finger position presented by the finger position presentation image in step S11 is not determined to have been changed to the M-th finger position, the process proceeds to step S18, and the centralized processing unit 64 instructs the finger position presentation image generation unit 66 to change the finger position to be presented by the finger position presentation image. The process proceeds to step S19 from step S18.

In step S19, the centralized processing unit 64 counts the number d of the feature amounts (feature points) detected by the feature amount detection unit 62 while the finger position presented by the finger position presentation image 71 is not changed, and calculates a progress rate (d/D)×100 (percent) of the feature amount acquisition from the counted number d of the feature amounts and the predetermined comparison value D. Then, the centralized processing unit 64 supplies the calculated progress rate of the feature amount acquisition to the acquisition status image generation unit 67. The acquisition status image generation unit 67 generates an acquisition status image that presents the acquisition status of the feature amount on the basis of the progress rate of the feature amount acquisition from the centralized processing unit 64, supplies it to the image output unit 24, and causes the display unit 15 to display it.

The process returns from step S19 to step S11, and the process from step S11 is repeated.

Furthermore, in a case where the finger position presentation image generation unit 66 is instructed to change the finger position by the centralized processing unit 64 in step S18, the process returns to step S11, and the finger position presentation image generation unit 66 generates a finger position presentation image in which the finger position is changed, supplies it to the image output unit 24, and causes the display unit 15 to display the finger position presentation image in which the finger position is changed.

Furthermore, in a case where the fingerprint images of all portions of the fingerprint are determined to have been obtained in step S17, that is, in a case where the finger position presented by the finger position presentation image in step S11 is determined to have been changed to the M-th finger position, the process is terminated.

Exemplary Configuration of Fingerprint Authentication Processing Unit 23

Next, the fingerprint authentication processing unit 23 in FIG. 1 will be described.

Figure 25:
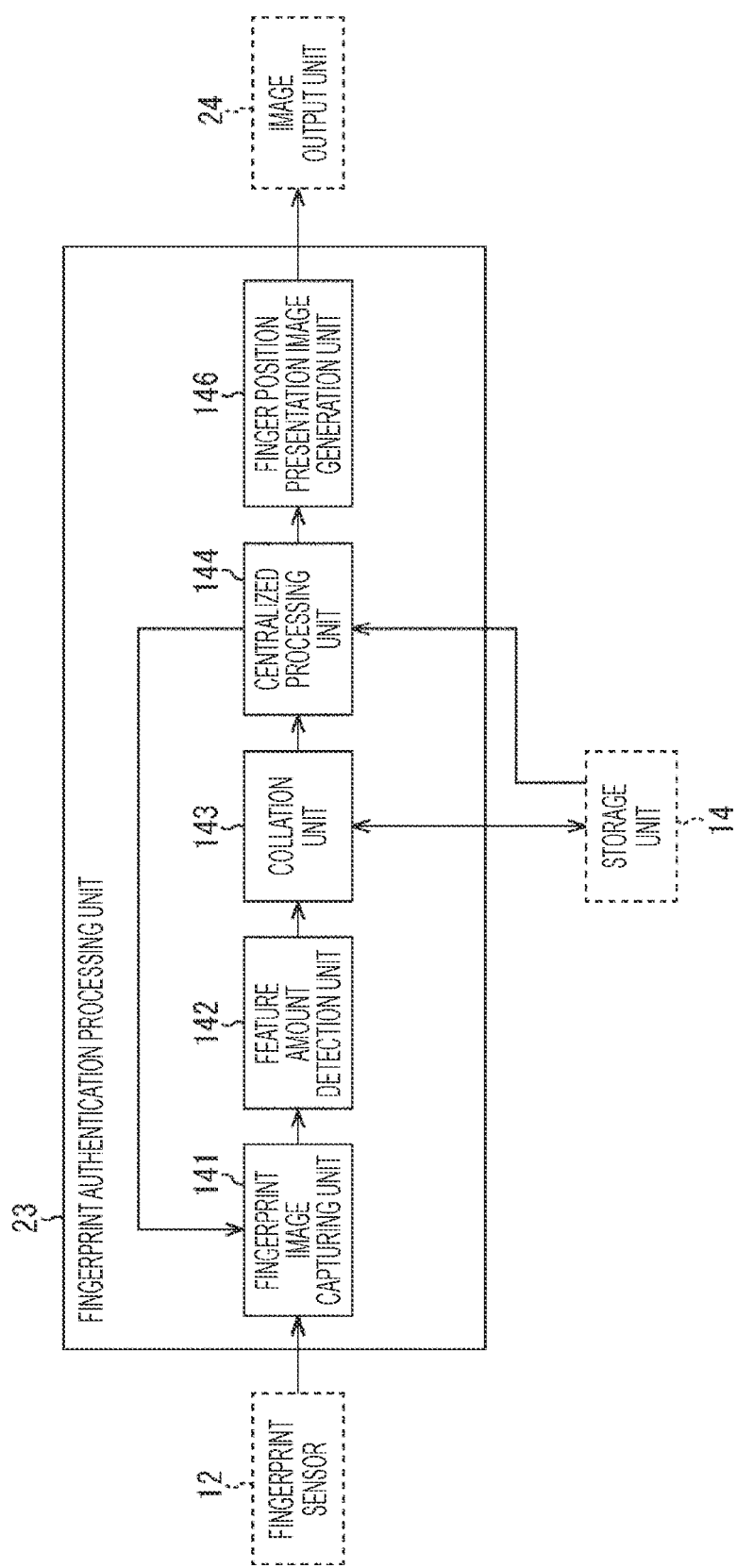
FIG. 25 is a block diagram illustrating an exemplary configuration of a fingerprint authentication processing unit.

FIG. 25 is a block diagram illustrating an exemplary configuration of the fingerprint authentication processing unit 23.

In FIG. 25, the fingerprint authentication processing unit 23 includes a fingerprint image capturing unit 141, a feature amount detection unit 142, a collation unit 143, a centralized processing unit 144, and a finger position presentation image generation unit 146.

The fingerprint image capturing unit 141 captures a fingerprint image from the fingerprint sensor 12 on the basis of an instruction from the centralized processing unit 144, and supplies it to the feature amount detection unit 142.

The feature amount detection unit 142 extracts multiple feature points (minutiae) included in the fingerprint on the basis of the fingerprint image from the fingerprint image capturing unit 141, and detects a feature amount indicating a position and a direction of each feature point. The feature amount detection unit 142 supplies each detected feature amount to the collation unit 143.

The collation unit 143 reads the template generated by the fingerprint registration processing unit 22 in FIG. 5 from the storage unit 14, and collates the feature amount registered as a template with the feature amount from the feature amount detection unit 142. Then, in a case where a degree of matching between the feature amount registered as a template and the feature amount from the feature amount detection unit 142 (hereinafter also referred to as a detected feature amount) is equal to or higher than a predetermined threshold value, for example, the collation unit 143 determines that the detected feature amount matches the template, and determines that the detected feature amount does not match the template in a case where it is less than the threshold value. Then, the collation unit 143 supplies a collation result as to whether the detected feature amount matches the template to the centralized processing unit 144.

The centralized processing unit 144 reads the template from the storage unit 14, and instructs the finger position presentation image generation unit 146 regarding the finger position to be presented by the finger position presentation image in such a manner that the fingerprint sensor 12 obtains the fingerprint image in the range of fingerprints in which a large amount of feature amounts as the template is distributed.

The finger position presentation image generation unit 146 generates a finger position presentation image that presents the finger position instructed by the centralized processing unit 144, supplies it to the image output unit 24, and causes the display unit 15 to display it.

<Details of Fingerprint Authentication Process>

Next, details of the fingerprint authentication process will be described.

Figure 26:
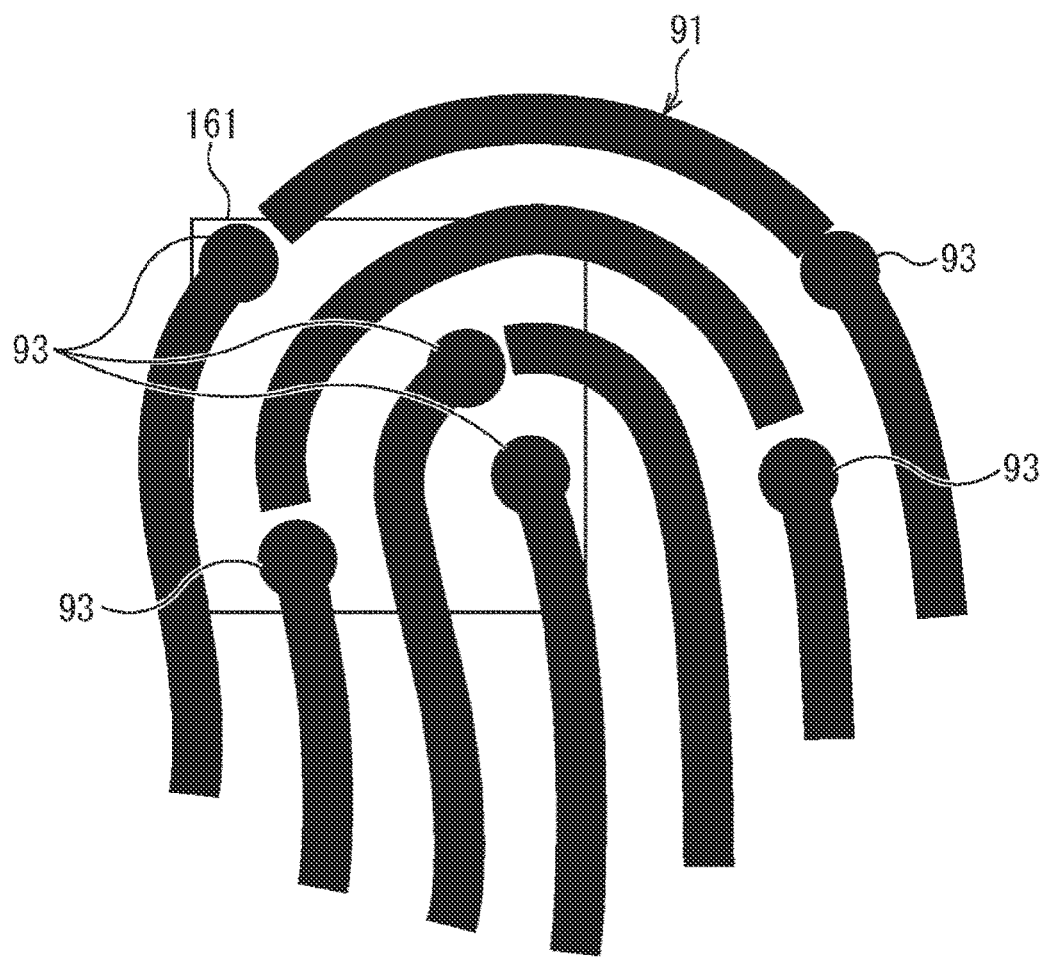
FIG. 26 is a diagram exemplifying a distribution of positions of feature amounts (feature points) of a fingerprint registered as a template.

FIG. 26 is a diagram exemplifying a distribution of positions of feature amounts (feature points) of the fingerprint registered in the template. In FIG. 26, the fingerprint 91 is a diagram illustrating the fingerprint of the user with the feature amount registered as a template. The feature point 93 is a feature point at which the feature amount as a template is detected. A fingerprint image acquisition range 161 indicates a range of the fingerprint image obtained by the detection area 12A of the fingerprint sensor 12.

When the fingerprint authentication process starts, the centralized processing unit 144 in FIG. 25 reads the template stored in the storage unit 14, and grasps the distribution of positions of the feature points 93 at which the feature amounts as the template have been detected. Then, the centralized processing unit 144 detects, as an appropriate position of the fingerprint image acquisition range 161, a position of the fingerprint image acquisition range 161 at which the number of the feature points 93 included in the fingerprint image acquisition range 161 is maximized or a position of the fingerprint image acquisition range 161 at which the number of the feature points 93 included in the fingerprint image acquisition range 161 is equal to or higher than a predetermined threshold value on the basis of the distribution of positions of the feature points 93.

Furthermore, the centralized processing unit 144 obtains the finger position at which the appropriate position of the fingerprint image acquisition range 161 is the contact portion of the fingerprint with respect to the detection area 12A of the fingerprint sensor 12. Then, the centralized processing unit 144 instructs the finger position presentation image generation unit 146 to generate a finger position presentation image that presents the obtained finger position.

The finger position presentation image generation unit 146 generates a finger position presentation image that presents the finger position instructed by the centralized processing unit 144, supplies it to the image output unit 24, and causes the display unit 15 to display it.

Figure 27:
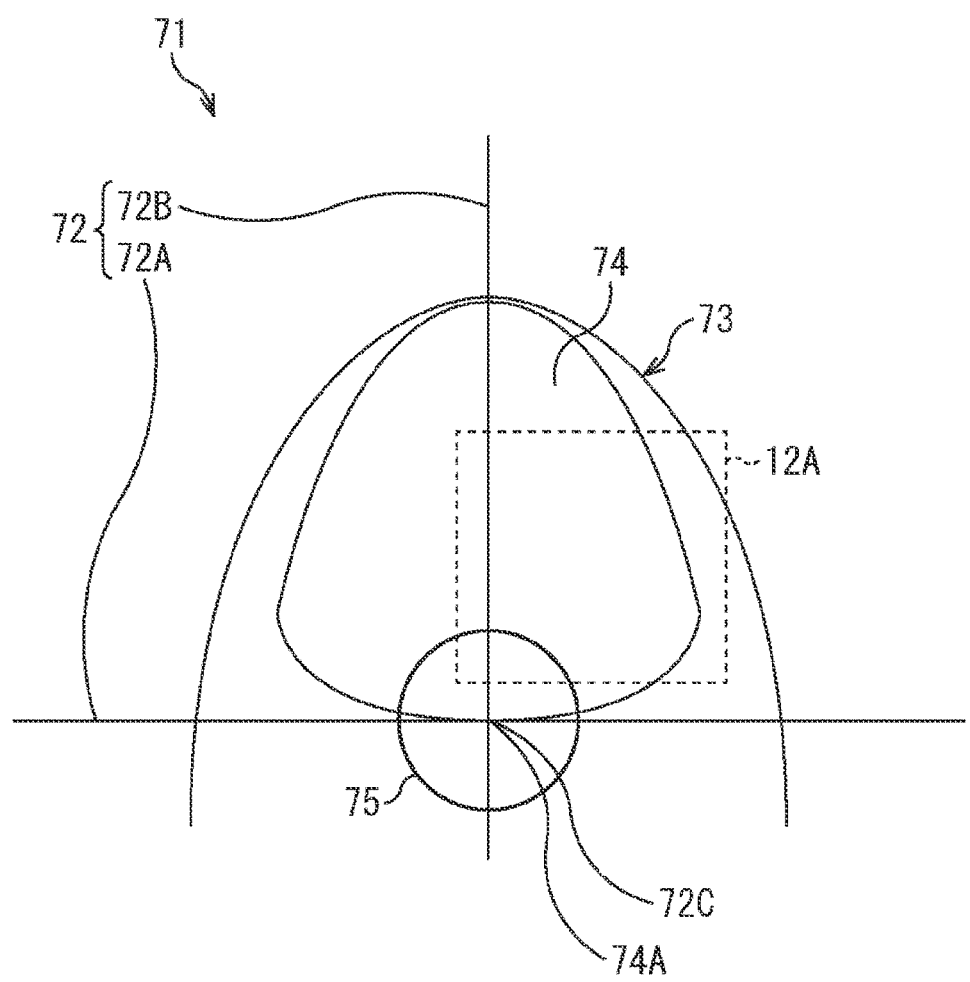
FIG. 27 is a diagram exemplifying a finger position presentation image to be displayed on the display unit at a time of fingerprint authentication.

FIG. 27 is a diagram exemplifying the finger position presentation image to be displayed on the display unit 15 at the time of fingerprint authentication. Note that, since the finger position presentation image 71 of FIG. 27 is the same as the finger position presentation image 71 in FIGS. 6A, 6B and 6C and the like, parts corresponding to those of the finger position presentation image 71 in FIGS. 6A, 6B and 6C are denoted by the same reference signs, and descriptions thereof will be omitted.

The finger position presented by the finger position presentation image 71 in FIG. 27 is a position corresponding to a case where the position of the fingerprint image acquisition range 161 in FIG. 26 is detected as an appropriate position. The finger position reference point 72C of the finger position presentation image 71 is displayed at a diagonally lower left position with respect to the central position of the detection area 12A. When the user touches the finger position presented by this finger position presentation image 71 with the finger, the fingerprint image in the fingerprint image acquisition range 161 in FIG. 26 is obtained by the fingerprint sensor 12. Since the fingerprint image obtained by the fingerprint sensor 12 has a large number of feature amounts, it is possible to suppress an authentication error in the collation unit 143 in FIG. 5.

Figure 28:
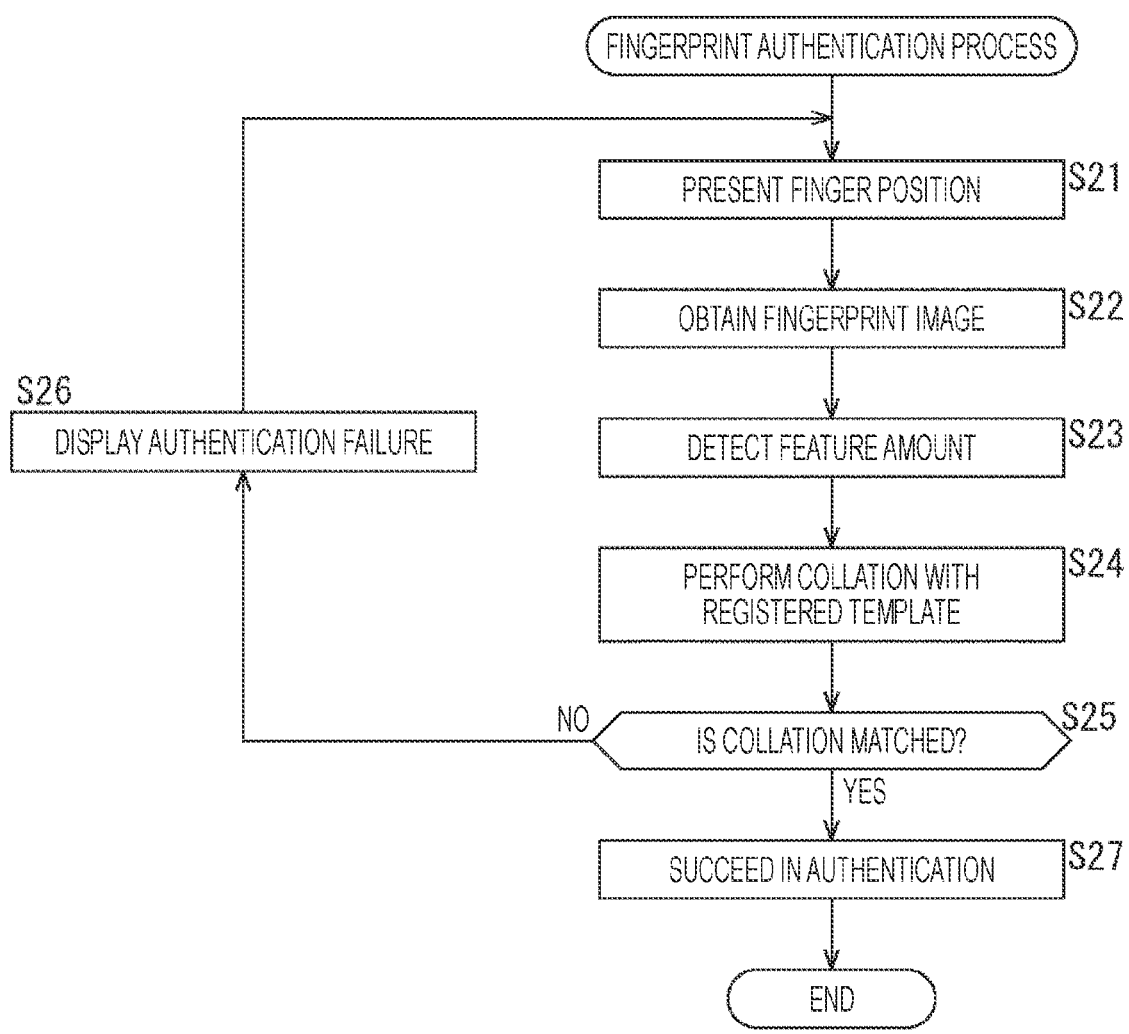
FIG. 28 is a flowchart for explaining an exemplary fingerprint authentication process performed by the fingerprint authentication processing unit.

FIG. 28 is a flowchart for explaining an exemplary fingerprint authentication process performed by the fingerprint authentication processing unit 23 in FIG. 25.

In step S21, the finger position presentation image generation unit 146 generates a finger position presentation image that presents the finger position instructed by the centralized processing unit 144, supplies it to the image output unit 24, and causes the display unit 15 to display it. Note that the centralized processing unit 144 instructs the finger position presentation image generation unit 146 regarding the finger position to be presented by the finger position presentation image on the basis of the distribution of positions of the feature amounts (feature points) as a template. Furthermore, in a case where, for example, authentication failure continues and the processing of step S21 is repeated multiple times, the centralized processing unit 144 may instruct the finger position presentation image generation unit 146 to change the finger position to be presented by the finger position presentation image. The process proceeds to step S22 from step S21. The user touches the finger position presented by the finger position presentation image displayed on the display unit 15 with the finger.

In step S22, the fingerprint image capturing unit 141 obtains a fingerprint image from the fingerprint sensor 12, and supplies it to the feature amount detection unit 142. The process proceeds to step S23 from step S22.

In step S23, the feature amount detection unit 142 extracts the feature points (end points and branching points of ridges of the fingerprint) on the basis of the fingerprint image supplied from the fingerprint image capturing unit 141 in step S22, and detects the position and direction of the feature points as a detected feature amount. Note that the feature amount detection process in the feature amount detection unit 142 is the same as the feature amount detection process in the feature amount detection unit 62 of the fingerprint registration processing unit 22 in FIG. 5, and thus descriptions thereof will be omitted. The feature amount detection unit 142 supplies the detected feature amount to the collation unit 143. The process proceeds to step S24 from step S23.

In step S24, the collation unit 143 collates the detected feature amount supplied from the feature amount detection unit 142 in step S23 with the feature amount as a template stored in the storage unit 14, and supplies a collation result to the centralized processing unit 144. The process proceeds to step S25 from step S24.

In step S25, the centralized processing unit 144 determines whether or not the detected feature amount matches the template on the basis of the collation result supplied from the collation unit 143 in step S24.

In a case where it is determined in step S25 that the detected feature amount does not match the template, the process proceeds to step S26, and the centralized processing unit 64 causes the finger position presentation image generation unit 146 (or an image generation unit (not illustrated)) to generate a presentation image that presents authentication failure, and causes the display unit 15 to display it. The process returns from step S26 to step S21, and the process of steps S21 to S25 is repeated.

Furthermore, in a case where it is determined in step S25 that the detected feature amount matches the template, the process proceeds to step S27, and the centralized processing unit 144 causes the finger position presentation image generation unit 146 (or the image generation unit (not illustrated)) to generate a notification image that makes notification of authentication success, and causes the display unit 15 to display it. The fingerprint authentication process is then terminated.

According to the fingerprint authentication process of the fingerprint authentication processing unit 23 described above, the user is enabled to easily and accurately touch the finger position presented by the finger position presentation image 71 in a similar manner to the case of the fingerprint registration process, thereby facilitating acquisition of the fingerprint information (feature amount) in the intended range of the fingerprint. Therefore, the time required to authenticate the fingerprint and the number of times of touching by changing the finger position are reduced, and fingerprint authentication is performed efficiently.

Note that, in the fingerprint authentication process, the finger position to be presented by the finger position presentation image 71 may be changed in a similar manner to the fingerprint registration process, and the feature amount of a wide-range portion of the entire range of the fingerprint may be obtained to perform the authentication process. In this case, with the finger position presented by the finger position presentation image 71, the user is enabled to easily and accurately touch the presented position, thereby facilitating acquisition of the fingerprint information (feature amount) in the intended range of the fingerprint. Therefore, the time required for authentication and the number of times of touching by changing the finger position are reduced, and fingerprint authentication is performed efficiently.

Furthermore, in the fingerprint authentication process, the acquisition status of the feature amount may be presented as in the acquisition status images 106 to 108 in FIGS. 20, 21A, 21B, 22A, 22B, 22C, 22D and 22E in a similar manner to the case of the fingerprint registration process. In this case, the user is enabled to grasp the acquisition status of the feature amount so that the shift (change of the touch position) of the position at which the feature amount is obtained can be performed smoothly in a case of performing the shift, whereby the time required to register the fingerprint can be reduced. Furthermore, the user is enabled to intuitively grasp in which part of the fingerprint range the feature amount has not been obtained, and the position to be touched is changed efficiently. Furthermore, with the acquisition status of the feature amount fed back to the user in real time, it becomes possible to accurately present the presence/absence of the feature amount acquisition to the user, and to prompt the user to improve the way of touching. Moreover, with the acquisition status image 108 as illustrated in FIGS. 22A, 22B, 22C, 22D and 22E displayed, it becomes possible to reduce the inconvenience of the authentication.

<Computer>

The series of processes in the processing unit 16, the processing switching unit 21, the fingerprint registration processing unit 22, the fingerprint authentication processing unit 23, and the image output unit 24 described above may be executed by hardware, or may be executed by software. In a case of executing the series of processes by software, a program constituting the software is installed in a computer. Here, examples of the computer include a computer incorporated in dedicated hardware, a general-purpose personal computer capable of implementing various functions by installing various programs, and the like.

Figure 29:
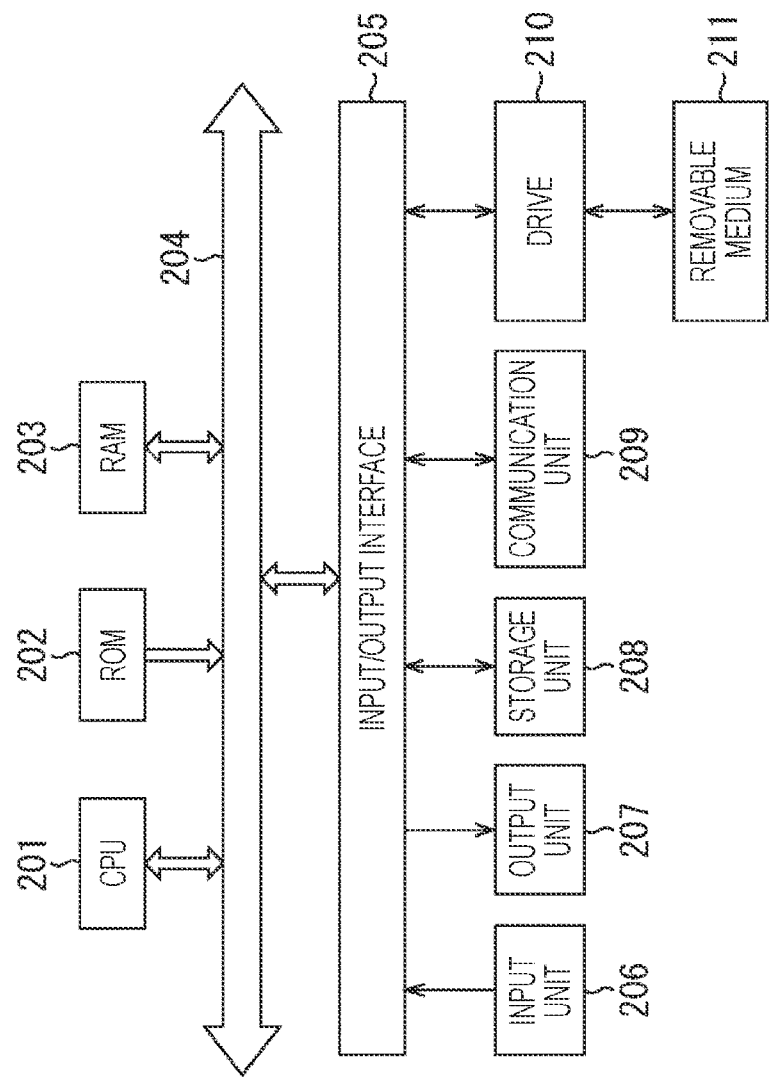
FIG. 29 is a block diagram illustrating an exemplary hardware configuration of a computer that executes, using a program, a series of processes.

FIG. 29 is a block diagram illustrating an exemplary hardware configuration of a computer that executes, using a program, the series of processes described above.

In the computer, a central processing unit (CPU) 201, a read only memory (ROM) 202, and a random access memory (RAM) 203 are coupled to one another via a bus 204.

An input/output interface 205 is further connected to the bus 204. An input unit 206, an output unit 207, a storage unit 208, a communication unit 209, and a drive 210 are connected to the input/output interface 205.

The input unit 206 includes a keyboard, a mouse, a microphone, and the like. The output unit 207 includes a display, a speaker, and the like. The storage unit 208 includes a hard disk, a non-volatile memory, and the like. The communication unit 209 includes a network interface, and the like. The drive 210 drives a removable medium 211 such as a magnetic disk, an optical disk, a magneto-optical disk, or a semiconductor memory.

In the computer configured as described above, for example, the CPU 201 loads the program stored in the storage unit 208 into the RAM 203 via the input/output interface 205 and the bus 204 and executes the program, thereby performing the series of processes described above.

The program to be executed by the computer (CPU 201) may be provided by, for example, being recorded in the removable medium 211 as a package medium or the like. Furthermore, the program may be provided through a wired or wireless transmission medium such as a local area network, the Internet, or digital satellite broadcasting.

In the computer, the program may be installed in the storage unit 208 via the input/output interface 205 by attaching the removable medium 211 to the drive 210. Furthermore, the program may be received by the communication unit 209 via a wired or wireless transmission medium and installed in the storage unit 208. In addition, the program may be installed in the ROM 202 or the storage unit 208 in advance.

Note that the program to be executed by the computer may be a program in which processing is executed in a time-series manner according to the order described in the present specification, or may be a program in which processing is executed in parallel or at a necessary timing such as when a call is made.

Note that the present technology may also employ the following configurations.

<1> A fingerprint authentication device including:

a display control unit that generates a presentation image for presenting a position of a nail root of a finger at a time of detecting a fingerprint; and a processing unit that obtains an image of the fingerprint using the generated presentation image.

<2> The fingerprint authentication device according to <1>, in which the presentation image includes a cross image in a shape of a cross.

<3> The fingerprint authentication device according to <1>, in which the presentation image includes an image of a nail.

<4> The fingerprint authentication device according <1>, in which the presentation image includes an image of a fingertip including an image of a nail.

<5> The fingerprint authentication device according to <1>, in which the presentation image includes a circular image in a shape of a circle.

<6> The fingerprint authentication device according to <1>, in which
the presentation image includes an image in which at least any two images of a cross image in a shape of a cross, an image of a nail, or a circular image in a shape of a circle are superimposed.

<7> The fingerprint authentication device according to <1>, in which
the presentation image includes an image in which at least any two images of a cross image in a shape of a cross, an image of a nail, or a circular image in a shape of a circle are superimposed in a stepwise manner.

<8> The fingerprint authentication device according to any one of <1> to <7>, in which
the position of the nail root to be presented is displaced to a plurality of positions.

<9> The fingerprint authentication device according to any one of <1> to <8>, in which
the display control unit is configured to generate:
an image of a detection area for detecting the fingerprint; and
the presentation image that presents the position of the nail root on the image of the detection area.

<10> The fingerprint authentication device according to any one of <1> to <9>, further including:
a display unit that displays the presentation image generated by the display control unit.

<11> The fingerprint authentication device according to <10>, in which
the display control unit displays the presentation image superimposed on a detection area for detecting the fingerprint.

<12> The fingerprint authentication device according to any one of <1> to <11>, further including:
an acquisition status image generation unit that generates an acquisition status image for presenting an acquisition status of fingerprint information from the fingerprint.

<13> The fingerprint authentication device according to <12>, in which
the acquisition status image includes an image with sharpness that changes according to a progress rate of acquisition of the fingerprint information.

<14> The fingerprint authentication device according to <12> or <13>, in which
the acquisition status image includes an image for presenting a position of an area of the fingerprint where acquisition of the fingerprint information is performed.

<15> A fingerprint authentication method for a fingerprint authentication device including:
a display control unit; and
a processing unit, the method including:
generating, using the display control unit, a presentation image for presenting a position of a nail root of a finger at a time of detecting a fingerprint; and
obtaining, using the processing unit, an image of the fingerprint using the generated presentation image.

<16> A program causing a computer to function as:
a display control unit that generates a presentation image for presenting a position of a nail root of a finger at a time of detecting a fingerprint; and
a processing unit that obtains an image of the fingerprint using the generated presentation image.

REFERENCE SIGNS LIST

11 Fingerprint authentication device
12 Fingerprint sensor
13 Operation input unit
14 Storage unit
15 Display unit
16 Processing unit
21 Processing switching unit
22 Fingerprint registration processing unit
23 Fingerprint authentication processing unit
24 Image output unit
61 Fingerprint image capturing unit
62 Feature amount detection unit
63 Collation unit
64 Centralized processing unit
65 Fingerprint image combining unit
66 Finger position presentation image generation unit
67 Acquisition status image generation unit

The invention claimed is:

1. A fingerprint authentication device, comprising:
a display control unit configured to generate a presentation image that presents a position of a nail root of a finger at a time of detection of a fingerprint, wherein
the generated presentation image includes an image in which at least two images of a cross image in a shape of a cross, an image of a nail, or a circular image in a shape of a circle are superimposed,
the nail root coincides with a reference point in the cross image, and
the reference point in the cross image corresponds to a center of the circular image; and
a processing unit configured to obtain an image of the fingerprint based on the generated presentation image.

2. The fingerprint authentication device according to claim 1, wherein the generated presentation image further includes the cross image in the shape of the cross.

3. The fingerprint authentication device according to claim 1, wherein the generated presentation image further includes the image of the nail.

4. The fingerprint authentication device according to claim 1, wherein
the generated presentation image further includes an image of a fingertip, and
the image of the fingerprint includes the image of the nail.

5. The fingerprint authentication device according to claim 1, wherein the generated presentation image further includes the circular image in the shape of the circle.

6. The fingerprint authentication device according to claim 1, wherein the generated presentation image includes the image in which the at least two images of the cross image in the shape of the cross, the image of the nail, or the circular image in the shape of the circle are superimposed in a stepwise manner.

7. The fingerprint authentication device according to claim 1, wherein the position of the nail root is displaced to a plurality of positions in the generated presentation image.

8. The fingerprint authentication device according to claim 1, wherein
the display control unit is further configured to generate an image of a detection area for the detection of the fingerprint, and
the generated presentation image further presents the position of the nail root on the image of the detection area.

9. The fingerprint authentication device according to claim 1, further comprising a display unit configured to display the generated presentation image.

10. The fingerprint authentication device according to claim 9, wherein
the display control unit is further configured to display the generated presentation image superimposed on an image of a detection area, and
the detection area is for the detection of the fingerprint.

11. The fingerprint authentication device according to claim 1, further comprising an acquisition status image generation unit configured to generate an acquisition status image that presents an acquisition status of fingerprint information from the fingerprint.

12. The fingerprint authentication device according to claim 11, wherein
the processing unit is further configured to obtain a progress rate of acquisition of the fingerprint information, and
the acquisition status image includes an image with sharpness that changes based on the progress rate of the acquisition of the fingerprint information.

13. The fingerprint authentication device according to claim 12, wherein
the processing unit is further configured to determine the progress rate is less than a threshold value, and
the acquisition status image generation unit is further configured to generate an error image based on the determination that the progress rate is less than the threshold value.

14. The fingerprint authentication device according to claim 13, wherein the error image includes a cross mark on the image of the fingerprint.

15. The fingerprint authentication device according to claim 11, wherein the acquisition status image includes an image that presents a position of an area of the fingerprint where acquisition of the fingerprint information is performed.

16. A fingerprint authentication method, comprising:
in a fingerprint authentication device including a display control unit and a processing unit:
generating, by the display control unit, a presentation image for presenting a position of a nail root of a finger at a time of detecting a fingerprint, wherein
the generated presentation image includes an image in which at least two images of a cross image in a shape of a cross, an image of a nail, or a circular image in a shape of a circle are superimposed,
the nail root coincides with a reference point in the cross image, and
the reference point in the cross image corresponds to a center of the circular image; and
obtaining, by the processing unit, an image of the fingerprint based on the generated presentation image.

17. A non-transitory computer-readable medium having stored thereon, computer-executable instructions which, when executed by a processor, cause the processor to execute operations, the operations comprising:
generating a presentation image for presenting a position of a nail root of a finger at a time of detecting a fingerprint; wherein
the generated presentation image includes an image in which at least two images of a cross image in a shape of a cross, an image of a nail, or a circular image in a shape of a circle are superimposed,
the nail root coincides with a reference point in the cross image, and
the reference point in the cross image corresponds to a center of the circular image; and
obtaining an image of the fingerprint based on the generated presentation image.

* * * * *